United States Patent [19]
Fujii et al.

[11] Patent Number: 5,658,777
[45] Date of Patent: Aug. 19, 1997

[54] ALCOHOL ACETYLTRANSFERASE GENES AND USE THEREOF

[75] Inventors: Toshio Fujii; Akihiro Iwamatsu; Hiroyuki Yoshimoto, all of Tokyo-To; Toshitaka Minetoki, Nishinomiya; Takayuki Bogaki, Nishinomiya; Naoshi Nagasawa, Nishinomiya, all of Japan

[73] Assignee: Kirin Beer Kabushiki Kaisha, Tokyo-To, Japan

[21] Appl. No.: 461,599

[22] Filed: Jun. 5, 1995

Related U.S. Application Data

[62] Division of Ser. No. 77,939, Jun. 18, 1993, Pat. No. 5,521,088.

[30] Foreign Application Priority Data

Jun. 18, 1992 [JP] Japan ................................. 4-184328
Feb. 26, 1993 [JP] Japan ................................. 5-62997

[51] Int. Cl.$^6$ ................................. C12N 9/10; C07H 21/04
[52] U.S. Cl. ................. 435/172.3; 435/193; 536/23.2; 536/24.32
[58] Field of Search .................... 435/172.3, 193; 536/23.2, 24.32

[56] References Cited

U.S. PATENT DOCUMENTS 4,394,443  7/1983  Weissman ..................... 435/6

FOREIGN PATENT DOCUMENTS 9-106636  5/1991  WIPO.

OTHER PUBLICATIONS

Yoshioka et al., "Agric. Biol. Chem.", 45(10):2183–2190 (1981).
Akita et al., "Agric. Biol. Chem.", 54(6);1485–1490 (1990).
Malcorps et al., "Eur. J. Biochem.", 210:1015–1022 (1992).
Mauricio et al., "J. Argic. Food Chem.", 41:2086–2091 (1993).
Hewick et al., "J. Biol. Chem.", 256(15):7990–9777 (1981).
Hunkapiller et al., "Science", 226:304–311 (1984).
Chemical Abstracts No. 93765t, vol. 113, No. 11, Columbus, Ohio, US: Akita, Osamu, Suzuki, Syuzi Obata, Takaji, Hara, Shodo, "Purification and some properties of alcohol acetyltransferase from sake" (1990).
Biosis Previews Database, Philadelphia, US, Abstract No. 95066783, Malcorps P., Dufour, J–P., "Short–Chain and Medium–Chain Aliphatic Ester Synthesis in Sacchromyces–Cerevisiae". (1992).
Biosis Previews Database, Philadelphia, US Abstract No. 88025463, Yanaguichi T., Kiyokawa Y., Wakai Y., "Isolation of Sake–Yeast Strains Accumulating Large Amounts of Isoamyl Acetate." (1989).
Patent Abstracts of Japan, vol. 014, No. 192 (C–0711) (Apr. 19, 1990).
Malcorps P. et al.—"Short–chain & Medium–Chain aliphatic ester Synthesis in S. cerevisiae", Eur. J. Biochem. 210(3):1015–1022 (1992).

*Primary Examiner*—Robert A. Wax
*Assistant Examiner*—Einar Stole
*Attorney, Agent, or Firm*—Foley & Lardner

[57] ABSTRACT

This invention disclosed herein provides an alcohol acetyl transferase ("AATase"), an AATase encoding gene and a yeast having an improved ester producing ability due to transformation with the AATase encoding gene. This invention also provides a process for producing an alcoholic beverage having an enriched ester flavor using the transformed yeast.

8 Claims, 32 Drawing Sheets

FIG. 1(a)

```
  1       AG CGT GTG AGG ACT ACT CAT TGG CTT GCG ATT TAC GGT TTT TAT ATT        47
 48   TTT TGC CGC ACA TCA TTT TTT GGC CTG GTA TTG TCA TCG CGT TGA GCG           95
 96   GAC TCT GAA TAT AAT CCT ATT GTT TTT TAT GGA TCT CTG GAA GCG TCT          143
144   TTT TGA AGC CAA CCC AAC AAA AAT TCG AGA CAA GAA AAT AAA AAA CGG          191
                                                                  A
                                                                  ↓
192   CAC TTC ATC AGT ATC ACA AAT CAG GCC CCC GTG CAA CAA GAA TTA TCA GCT CTC ATG AAT   239
                                                                              Met Asn     2
240   GAA ATC GAT GAG AAA AAT CAG GCC CCC GTG CAA CAA GAA TGC CTG AAA          287
      Glu Ile Asp Glu Lys Asn Gln Ala Pro Val Gln Gln Glu Cys Leu Lys           18
        3
288   GAG ATG ATT CAG AAT GGG CAT GCT CGG CGT ATG GGA TCT GTT GAA GAT          335
      Glu Met Ile Gln Asn Gly His Ala Arg Arg Met Gly Ser Val Glu Asp           34
       19
```

FIG. 1(b)

```
336  CTG TAT GTT GCT CTC AAC AGA CAA AAC TTA TAT CGG AAC TTC TGC ACA  383
 35  Leu Tyr Val Ala Leu Asn Arg Gln Asn Leu Tyr Arg Asn Phe Cys Thr   50

384  TAT GGA GAA TTG AGT GAT TAC TGT ACT AGG GAT CAG CTC ACA TTA GCT  431
 51  Tyr Gly Glu Leu Ser Asp Tyr Cys Thr Arg Asp Gln Leu Thr Leu Ala   66

432  TTG AGG GAA ATC TGC CTG AAA AAT CCA ACT CTT TTA CAT ATT GTT CTA  479
 67  Leu Arg Glu Ile Cys Leu Lys Asn Pro Thr Leu Leu His Ile Val Leu   82

480  CCA ATA AGA TGG CCA AAT CAT GAA AAT TAT CGC AGT TCC GAA TAC       527
 83  Pro Ile Arg Trp Pro Asn His Glu Asn Tyr Arg Ser Ser Glu Tyr       98

528  TAT TCA CGG CCA CAT CCA GTG CAT GAT TAT ATT TCA GTA TTA CAG GAA  575
 99  Tyr Ser Arg Pro His Pro Val His Asp Tyr Ile Ser Val Leu Gln Glu  114

576  TTG AAA CTG AGT GGT GTG GTT CTC AAT GAA CAA CCT GAG TAC AGT GCA  623
115  Leu Lys Leu Ser Gly Val Val Leu Asn Glu Gln Pro Glu Tyr Ser Ala  130

624  GTA ATG AAG CAA ATA TTA GAA GAA TTC AAA AAT AGT AAG GGT TCC TAT  671
131  Val Met Lys Gln Ile Leu Glu Glu Phe Lys Asn Ser Lys Gly Ser Tyr  146
```

FIG. 1(c)

| | | | | | | | | | | | | | | | | |
|---|---|---|---|---|---|---|---|---|---|---|---|---|---|---|---|---|
| 672 | ACT | GCA | AAA | ATT | TTT | AAA | CTT | ACT | ACC | ACT | TTG | ACT | ATT | CCT | TAC | TTT | 719 |
| 147 | Thr | Ala | Lys | Ile | Phe | Lys | Leu | Thr | Thr | Thr | Leu | Thr | Ile | Pro | Tyr | Phe | 162 |
| 720 | GGA | CCA | ACA | GGA | CCG | AGT | TGG | CGG | CTA | ATT | TGT | CTT | CCA | GAA | GAG | CAC | 767 |
| 163 | Gly | Pro | Thr | Gly | Pro | Ser | Trp | Arg | Leu | Ile | Cys | Leu | Pro | Glu | Glu | His | 178 |
| 768 | ACA | GAA | AAG | TGG | AAA | AAA | TTT | ATC | TTT | GTA | TCT | AAT | CAT | TGC | ATG | TCT | 815 |
| 179 | Thr | Glu | Lys | Trp | Lys | Lys | Phe | Ile | Phe | Val | Ser | Asn | His | Cys | Met | Ser | 194 |
| 816 | GAT | GGT | CGG | TCT | TCG | ATC | CAC | TTT | TTT | CAT | GAT | TTA | AGA | GAC | GAA | TTA | 863 |
| 195 | Asp | Gly | Arg | Ser | Ser | Ile | His | Phe | Phe | His | Asp | Leu | Arg | Asp | Glu | Leu | 210 |
| 864 | AAT | AAT | ATT | AAA | ACT | CCA | CCA | AAA | AAA | TTA | GAT | TAC | ATT | TTC | AAG | TAC | 911 |
| 211 | Asn | Asn | Ile | Lys | Thr | Pro | Pro | Lys | Lys | Leu | Asp | Tyr | Ile | Phe | Lys | Tyr | 226 |
| 912 | GAG | GAT | TAC | CAA | TTG | AGG | AAA | CTT | CCA | GAA | CCG | ATC | GAA | AAG | 959 |
| 227 | Glu | Asp | Tyr | Gln | Leu | Arg | Lys | Leu | Pro | Glu | Pro | Ile | Glu | Lys | 242 |
| 960 | GTG | ATA | GAC | TTT | AGA | CCA | CCG | TAC | TTG | TTT | ATT | CCG | AAG | TCA | CTT | CTT | 1007 |
| 243 | Val | Ile | Asp | Phe | Arg | Pro | Pro | Tyr | Leu | Phe | Ile | Pro | Lys | Ser | Leu | Leu | 258 |

FIG. 1(d)

```
1008  TCG GGT TTC ATC TAC AAT CAT TTG AGA TTT TCT TCA AAA GGT GTC TGT  1055
259   Ser Gly Phe Ile Tyr Asn His Leu Arg Phe Ser Ser Lys Gly Val Cys  274

1056  ATG AGA ATG GAT GAT GTG GAA AAA ACC GAT GAT GTT GTC ACC GAG ATC  1103
275   Met Arg Met Asp Asp Val Glu Lys Thr Asp Asp Val Val Thr Glu Ile  290

1104  ATC AAT ATT TCA CCA ACA GAA TTT CAA GCG ATT AAA GCA AAT ATT AAA  1151
291   Ile Asn Ile Ser Pro Thr Glu Phe Gln Ala Ile Lys Ala Asn Ile Lys  306

1152  TCA AAT ATC CAA GGT AAG TGT ACT ATC ACT CCG TTT TTA CAT GTT TGT  1199
307   Ser Asn Ile Gln Gly Lys Cys Thr Ile Thr Pro Phe Leu His Val Cys  322

1200  TGG TTT GTA TCT CTT CAT AAA TGG GGT AAA TTT TTC AAA CCA TTG AAC  1247
323   Trp Phe Val Ser Leu His Lys Trp Gly Lys Phe Phe Lys Pro Leu Asn  338

1248  TTC GAA TGG CTT ACG GAT ATT TTT ATC CCC GCA GAT TGC CGC TCA CAA  1295
339   Phe Glu Trp Leu Thr Asp Ile Phe Ile Pro Ala Asp Cys Arg Ser Gln  354
```

FIG. 1(e)

```
1296  CTA CCA GAT GAT GAA ATG AGA CAG ATG TAC AGA TAT GGC GCT AAC  1343
 355  Leu Pro Asp Asp Glu Met Arg Gln Met Tyr Arg Tyr Gly Ala Asn   370

1344  GTT GGA TTT ATT GAC TTC ACC CCA TGG ATA AGC GAA TTT GAC ATG AAT  1391
 371  Val Gly Phe Ile Asp Phe Thr Pro Trp Ile Ser Glu Phe Asp Met Asn   386

1392  GAT AAC AAA GAA AAA TTT TGG CCA CTT ATT GAG CAC TAC CAT GAA GTA  1439
 387  Asp Asn Lys Glu Lys Phe Trp Pro Leu Ile Glu His Tyr His Glu Val   402

1440  ATT TCG GAA GCT TTA AGA AAT AAA AAG CAC CTC CAT GGC TTA GGG TTC  1487
 403  Ile Ser Glu Ala Leu Arg Asn Lys Lys His Leu His Gly Leu Gly Phe   418

1488  AAT ATA CAA GGC TTC GTT CAA AAA TAT GTG AAT ATT GAC AAG GTA ATG  1535
 419  Asn Ile Gln Gly Phe Val Gln Lys Tyr Val Asn Ile Asp Lys Val Met   434

1536  TGC GAT CGT GCC ATC GGG AAA AGA CGC GGA GGT ACA TTG TTA AGC AAT  1583
 435  Cys Asp Arg Ala Ile Gly Lys Arg Arg Gly Gly Thr Leu Leu Ser Asn   450

1584  GTA GGT CTG TTT AAT CAG TTA GAG GAG CCC GAT GCC AAA TAT TCT ATA  1631
 451  Val Gly Leu Phe Asn Gln Leu Glu Glu Pro Asp Ala Lys Tyr Ser Ile   466
```

FIG. 1(f)

```
1632 TGC GAT TTG GCA TTT CAA GGC CAA TTT GGC CAA GGA TCC TGG CAC CAA GCA TTT  1679
 467 Cys Asp Leu Ala Phe Gln Gly Gln Phe Gly Gln Gly Ser Trp His Gln Ala Phe   482

1680 TCC TTG GGT GTT TGT TCG ACT AAT GTA AAG GGG ATG AAT ATT GTT GTT            1727
 483 Ser Leu Gly Val Cys Ser Thr Asn Val Lys Gly Met Asn Ile Val Val            498

1728 GCT TCA ACA AAA AAT GTT GTT GGT AGC CAA GAA TCT CTC GAA GAG CTT            1775
 499 Ala Ser Thr Lys Asn Val Val Gly Ser Gln Glu Ser Leu Glu Glu Leu            514
                                                        B→

1776 TGC TCC ATT TAT AAA GCT CTC CTT TTA GGC CCT TAG ATC TCA CAT GAT            1823
 515 Cys Ser Ile Tyr Lys Ala Leu Leu Leu Gly Pro ***

1824 GCT TGA CTG ATA TTA TTC GAC AAT ATG ATT ATG TCG TGT AAA TAA CCC            1871

1872 ACT TTC ATG TTG TCA CTC CCT CGG CTT TGG TTG GTT AAA GGG ACT TAT            1919

1920 TGG T
```

FIG. 2(a)

```
1    GTA GCT TCA TTT GTT GGC ACA GGA CTA TTC CAC CCT TAG AAT TGA CTT    48
49   TTT GGA CAT TGA GCT AAG GTT CAA TGC ACT CGA TGG TCT TCT CAC TTC    96
97   CGA ATA TAT AGA TCT AGC GTG TGA GGA CTA CTC ATT GGC TTG CGA TTT    144
145  ACG GTT TTT ATA TTT TTT GCC GCA CAT CAT TTT TTG GCC TGG TAT TGT    192
193  CAT CGC GGT TGA GCG GAC TCT GAA TAT AAT CCT ATT GTT TTT TAT GGA    240
241  TCT CTG GAA GCG TCT TTT TGA AGC CAA CCC AAC AAA AAT TCG AGA CAA    288
289  GAA AAT AAA AAA CGG CAC TTC ATC AGT ATC ACA AAT ACC ATC AAT TTA    336
```

FIG. 2(b)

```
                    A
                    ↓
337  TCA GCT CTC ATG AAT GAA ATC GAT GAG AAA AAT CAG GCC CCC GTG CAA  384
                 Met Asn Glu Ile Asp Glu Lys Asn Gln Ala Pro Val Gln   13

385  CAA GAA TGC CTG AAA GAG ATG ATT CAG AAT GGG CAT GCT CGG CGT ATG  432
     Gln Glu Cys Leu Lys Glu Met Ile Gln Asn Gly His Ala Arg Arg Met   29

433  GGA TCT GTT GAA GAT CTG TAT GTT GCT CTC AAC AGA CAA AAC TTA TAT  480
     Gly Ser Val Glu Asp Leu Tyr Val Ala Leu Asn Arg Gln Asn Leu Tyr   45

481  CGA AAC TTC TGC ACA TAT GGA GAA TTG AGT GAT TAC TGT ACT AGG GAT  528
     Arg Asn Phe Cys Thr Tyr Gly Glu Leu Ser Asp Tyr Cys Thr Arg Asp   61

529  CAG CTC ACA TTA GCT TTG AGG GAA ATC TGC CTG AAA AAT CCA ACT CTT  576
     Gln Leu Thr Leu Ala Leu Arg Glu Ile Cys Leu Lys Asn Pro Thr Leu   77

577  TTA CAT ATT GTT CTA CCA ACA AGA TGG CCA AAT CAT GAA AAT TAT TAT  624
     Leu His Ile Val Leu Pro Thr Arg Trp Pro Asn His Glu Asn Tyr Tyr   93

625  CGC AGT TCC GAA TAC TAT TCA CGG CCA CAT CCA GTG CAT GAT TAT ATC  672
     Arg Ser Ser Glu Tyr Tyr Ser Arg Pro His Pro Val His Asp Tyr Ile  109
```

FIG. 2(c)

```
673  TCA GTA TTA CAA GAA TTG AAA CTG AGT GGT GTG GTT CTC AAT GAA CAA  720
110  Ser Val Leu Gln Glu Leu Lys Leu Ser Gly Val Val Leu Asn Glu Gln  125

721  CCT GAG TAC AGT GCA GTA ATG AAG CAA ATA TTA GAA GAA TTC AAA AAT  768
126  Pro Glu Tyr Ser Ala Val Met Lys Gln Ile Leu Glu Glu Phe Lys Asn  141

769  AGT AAG GGT TCC TAT ACT GCA AAA ATT TTT AAA CTT ACT ACC ACT TTG  816
142  Ser Lys Gly Ser Tyr Thr Ala Lys Ile Phe Lys Leu Thr Thr Thr Leu  157

817  ACT ATT CCT TAC TTT GGA CCA ACA GGA CCG AGT TGG CGG CTA ATT TGT  864
158  Thr Ile Pro Tyr Phe Gly Pro Thr Gly Pro Ser Trp Arg Leu Ile Cys  173

865  CTT CCA GAA GAG CAC ACA GAA AAG TGG AGA AAA TTT ATC TTT GTA TCT  912
174  Leu Pro Glu Glu His Thr Glu Lys Trp Arg Lys Phe Ile Phe Val Ser  189

913  AAT CAT TGC ATG TCT GAT GGT CGG TCT TCG ATC CAC TTT TTT CAT GAT  960
190  Asn His Cys Met Ser Asp Gly Arg Ser Ser Ile His Phe Phe His Asp  205

961  TTA AGA GAC GAA TTA AAT AAT ATT AAA ACT CCA AAA AAA TTA GAT       1008
206  Leu Arg Asp Glu Leu Asn Asn Ile Lys Thr Pro Lys Lys Leu Asp      221
```

FIG. 2(d)

```
1009  TAC ATT TTC AAG TAC GAG GAT TAC CAA TTA TTG AGG AAA CTT CCA  1056
 222  Tyr Ile Phe Lys Tyr Glu Asp Tyr Gln Leu Leu Arg Lys Leu Pro   237

1057  GAA CCG ATC GAA AAG GTG ATA GAC TTT AGA CCA CCG TAC TTG TTT ATT  1104
 238  Glu Pro Ile Glu Lys Val Ile Asp Phe Arg Pro Pro Tyr Leu Phe Ile   253

1105  CCG AAG TCA CTT CTT TCG GGT TTC ATC TAC AAT CAT TTG AGA TTT TCT  1152
 254  Pro Lys Ser Leu Leu Ser Gly Phe Ile Tyr Asn His Leu Arg Phe Ser   269

1153  TCA AAA GGT GTC TGT ATG AGA ATG GAT GAT GTG GAA AAA ACC GAT GAT  1200
 270  Ser Lys Gly Val Cys Met Arg Met Asp Asp Val Glu Lys Thr Asp Asp   285

1201  GTT GTC ACC GAG ATC ATC AAT ATT TCA CCA ACA GAA TTT CAA GCG ATT  1248
 286  Val Val Thr Glu Ile Ile Asn Ile Ser Pro Thr Glu Phe Gln Ala Ile   301

1249  AAA GCA AAT ATT AAA TCA AAT ATC CAA GGT AAG TGT ACT ATC ACT CCG  1296
 302  Lys Ala Asn Ile Lys Ser Asn Ile Gln Gly Lys Cys Thr Ile Thr Pro   317

1297  TTT TTA CAT GTT TGT TGG TTT GTA TCT CTT CAT AAA TGG GGT AAA TTT  1344
 318  Phe Leu His Val Cys Trp Phe Val Ser Leu His Lys Trp Gly Lys Phe   333
```

FIG. 2(e)

```
1345  TTC AAA CCA TTG GAA TGG AAC TTC GAA TGG AAC TTC GAA TGG AAC CTT ACG GAT ATT TTT ATC CCC GCA  1392
334   Phe Lys Pro Leu Glu Trp Asn Phe Glu Trp Leu Thr Asp Ile Phe Ile Pro Ala                      349

1393  GAT TGC CGC TCA CAA CTA CCA GAT GAT GAT GAA ATG AGA CAG ATG TAC  1440
350   Asp Cys Arg Ser Gln Leu Pro Asp Asp Asp Glu Met Arg Gln Met Tyr  365

1441  AGA TAT GGC GCT AAC GTT GGA TTT ATT GAC TTC ACC CCC TGG ATA AGC  1488
366   Arg Tyr Gly Ala Asn Val Gly Phe Ile Asp Phe Thr Pro Trp Ile Ser  381

1489  GAA TTT GAC ATG AAT GAT AAC AAA GAA AAT TTT TGG CCA CTT ATT GAG  1536
382   Glu Phe Asp Met Asn Asp Asn Lys Glu Asn Phe Trp Pro Leu Ile Glu  397

1537  CAC TAC CAT GAA GTA ATT TCG GAA GCT TTA AGA GGC TTC GTT CAA AAA AAG CAT CTC  1584
398   His Tyr His Glu Val Ile Ser Glu Ala Leu Arg Gly Phe Val Gln Lys Lys His Leu  413

1585  CAT GGC TTA GGG TTC AAT ATA CAA GGC ATC GGG AAA AGA TAT GTG AAC  1632
414   His Gly Leu Gly Phe Asn Ile Gln Gly Ile Gly Lys Arg Tyr Val Asn  429

1633  ATT GAC AAG GTA ATG TGC GAT CGT GCC ATC GGG AAA AGA CGC GGA GGT  1680
430   Ile Asp Lys Val Met Cys Asp Arg Ala Ile Gly Lys Arg Arg Gly Gly  445
```

FIG. 2(f)

```
1681  ACA TTG TTA AGC AAT GTA GGT CTG TTT AAT CAG TTA GAG GAG CCC GAT  1728
 446  Thr Leu Leu Ser Asn Val Gly Leu Phe Asn Gln Leu Glu Glu Pro Asp   461

1729  GCC AAA TAT TCT ATA TGC GAT TTG GCA TTT CAA GGA TCC                1776
 462  Ala Lys Tyr Ser Ile Cys Asp Leu Ala Phe Gln Gly Ser                 477

1777  TGG CAC CAA GCA TTT TCC TTG GGT GTT TGT TCG ACT AAT GTA AAG GGG   1824
 478  Trp His Gln Ala Phe Ser Leu Gly Val Cys Ser Thr Asn Val Lys Gly    493

1825  ATG AAT ATT GTT GTT GCT TCA ACA AAG AAT GTT GTT GGT AGT CAA GAA   1872
 494  Met Asn Ile Val Val Ala Ser Thr Lys Asn Val Val Gly Ser Gln Glu    509
                                                                    B →

1873  TCT CTC GAA GAG CTT TGC TCC ATT TAC AAA GCT CTC CTT TTA GGC CCT   1920
 510  Ser Leu Glu Glu Leu Cys Ser Ile Tyr Lys Ala Leu Leu Leu Gly Pro    525

1921  TAG ATC TCA CAT GAT GCT TGA CTG ATA TTA TTC GAC AAT ATG ATT ATG   1968
 526  ***

1969  TCG TGT
```

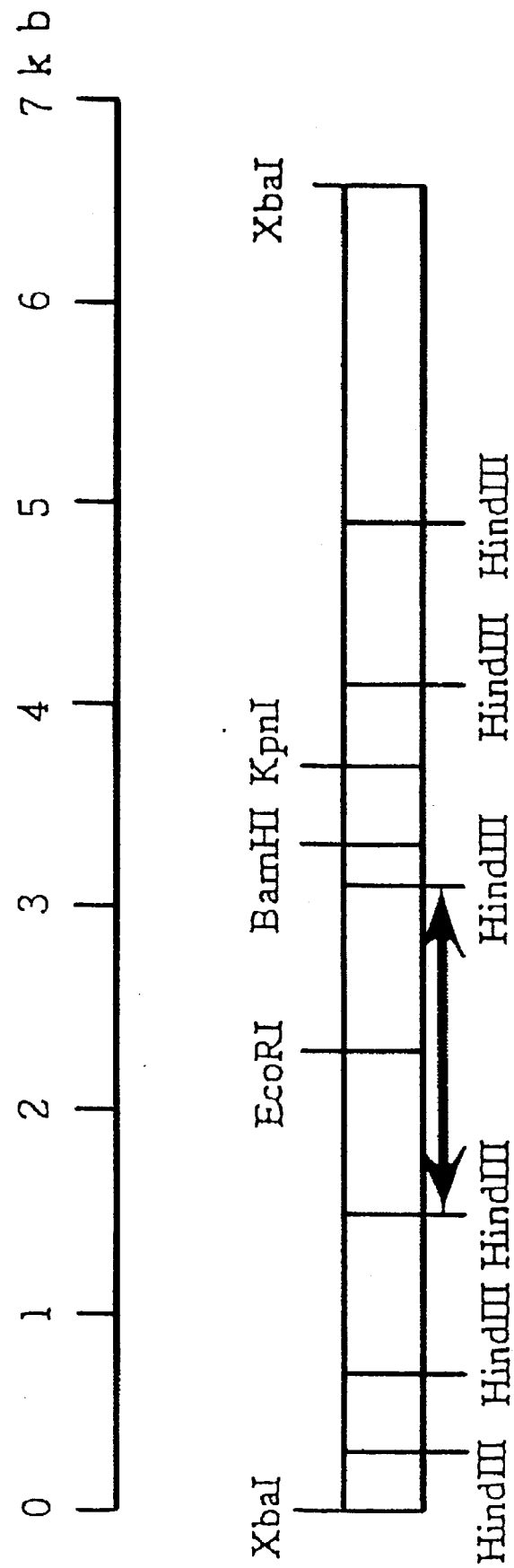
F I G. 3

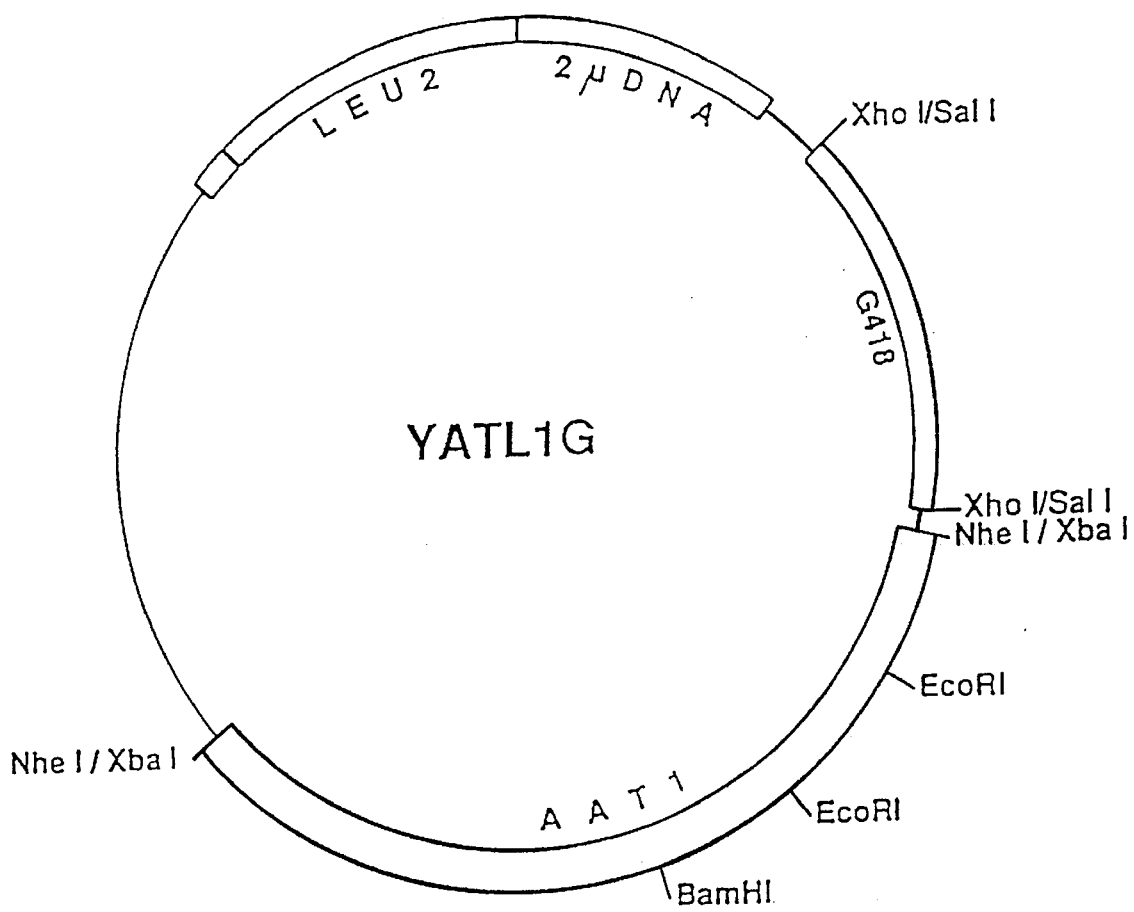
F I G. 15

FIG. 17(a)

```
         10         20         30         40         50         60
CTTGAACACATTGATCAATGTGAAATACTGATTGATGTTCAATATATTTGCTGATCTTAG 70         80         90        100        110        120
GGTGATTGGTAACCAAAAATGCCGTCGGGCATTGTTCTAAAGGCTTGTGATTTGTAAGT 130        140        150        160        170        180
TTTTGATCGCCTATTGTTTTTGGGCTGGCATCAGCATCGCGTGGAGCGAAGTCCAAATA 190        200        210        220        230        240
TGTTTCTATTGTTTTTCATGGCTCTCTTCGAGAAGCGTCTTTTTAAAGCCAACCCAACAA 250        260        270        280        290        300
AACTTGAGACATGGAAATACAGAAGAAAGCCAATTTAGCAGTATAACAAAATCATCAATCC
                A
                ↓
        310        320        330        340        350        360
AAAAACTCTAATGAATACCTACAGTGAAAAACGTCTCTTGTTCAAGATGAATGTCTTGT
                   MetAsnThrTyrSerGluLysThrSerLeuValGlnAspGluCysLeuVal
B
↓       370        380        390        400        410        420
CAAGATGATACAGAATGGGCATTCCCGGCTATGGGATCTGTGGAAGATTTGTACGCTGC
LysMetIleGlnAsnGlyHisSerArgArgMetGlySerValGluAspLeuTyrAlaAla
```

FIG. 17(b)

```
            430       440       450       460       470       480
ACTCAACAGACAGAAATTGTATCGGAATTTTTCGACATATTCAGAGCTGAATGATTACTG
LeuAsnArgGlnLysLeuTyrArgAsnPheSerThrTyrSerGluLeuAsnAspTyrCys 490       500       510       520       530       540
TACCAAAGATCAGCTCGCATTAGCTCTAAGAAATATGTTGAAAATCCGACTCTCCT
ThrLysAspGlnLeuLeuAlaLeuAlaLeuArgAsnIleCysLeuLysAsnProThrLeuLeu 550       560       570       580       590       600
ACATATTGTATTACCGGCAAGATCATGAAAAGTATTACCTTAGCTCAGAATA
HisIleValLeuProAlaArgTrpProAspHisGluLysTyrTyrLeuSerSerGluTyr 610       620       630       640       650       660
TTATTCAGCCCCGTCCAAAACATGATTATATTTCGGTTTTGCCTGAGTTGAAATTAGA
TyrSerGlnProArgProLysHisAspTyrIleSerValLeuProGluLeuLysLeuAsp 670       680       690       700       710       720
TGGTGTGATTCTCAACGAGCAACCTGAGCAACAATGCCCTAATGAAGCAAATACTAGAAGA
GlyValIleLeuAsnGluGlnProGluHisAsnAlaLeuMetLysGlnIleLeuGluGlu
```

FIG. 17(c)

```
             730        740        750        760        770        780
ATTTGCGAATAGCAATGGATCTTATACTGCAAAATCTTTAAATTGACCACCGCTTTGAC
PheAlaAsnSerAsnGlySerTyrThrAlaLysIlePheLysLeuThrThrAlaLeuThr 790        800        810        820        830        840
TATACCTTACACTGGGCCAACAAGTCCAACTTGGGGTTGATTTGTCTCCCAGAAGAAGA
IleProTyrThrGlyProThrSerProThrTrpArgLeuIleCysLeuProGluGluAsp 850        860        870        880        890        900
TGACACGAATAAGTGGAAGAAATTTATATTTGTATCCAATCACTGCCATGTGCGATGGTAG
AspThrAsnLysTrpLysLysPheIlePheValSerAsnHisCysMetCysAspGlyArg 910        920        930        940        950        960
ATCCTCAATTCACTTTTTCAGGATCTAAGAGATGAATTAAACACATAAAACTCTGCC
SerSerIleHisPhePheGlnAspLeuArgAspGluLeuAsnAsnIleLysThrLeuPro 970        980        990       1000       1010       1020
AAAGAAATTGGACTACATTTCGAGTACGAAAAGGATTACCAACTTTGAGAAAGCTCCC
LysLysLeuAspTyrIlePheGluTyrGluLysAspTyrGlnLeuLeuArgLysLeuPro 1030       1040       1050       1060       1070       1080
AGAACCCATTGAAAATATGATAGATTTCAGGCCCCATATTTGTTTATTCCGAAGTCTCT
GluProIleGluAsnMetIleAspPheArgProProTyrLeuPheIleProLysSerLeu
```

FIG. 17(d)

```
          1090      1100      1110      1120      1130      1140
TCTTTCTGGTTTTATTATTACAGTCATTTGAGTTTTCTCAAAGGGTGTTTGCACGAGAAT
 LeuSerGlyPheIleTyrSerHisLeuArgPheSerSerLysGlyValCysThrArgMet 1150      1160      1170      1180      1190      1200
GGATGAGATAGAAAAAGTGATGAGATTGTTACAGAATTATCAGAATATTTCTCCATCAGA
 AspGluIleGluLysSerAspGluIleValThrGluLeuIleIleAsnIleSerProSerGlu 1210      1220      1230      1240      1250      1260
GTTCAAAAATTAGAACGAAAATTAAACATTCCCGGTAAGTGCACCATCACTCC
 PheGlnLysIleArgThrLysIleLysLeuAsnIleProGlyLysCysThrIleThrPro 1270      1280      1290      1300      1310      1320
GTTCTTAGAAGTTTGTTGGTTTGTTACTCTCCATAAATGGGGCAAGTTTTTCAAACCACT
 PheLeuGluValCysTrpPheValThrLeuHisLysTrpGlyLysPhePheLysProLeu 1330      1340      1350      1360      1370      1380
GAAGTCGAGTGGCTCACTGATGTTTTATACCTGCAGATTGCCGCTCATTGCTGCCTGA
 LysPheGluTrpLeuThrAspValPheIleProAlaAspCysArgSerLeuLeuProGlu
```

FIG. 17(e)

```
      1390        1400        1410        1420        1430        1440
AGATGAAGAAGTGAGAGCTATGTACAGGTACGGCTAACGTTGGGTTTGTTGACTTCAC
AspGluValArgAlaMetTyrArgTyrGlyAlaAsnValGlyPheValAspPheThr 1450        1460        1470        1480        1490        1500
TCCATGGATAAGCAAATTCAACATGAACGACAGCAAAGAAAATTTCTGGCCACTTATTGC
ProTrpIleSerLysPheAsnMetAsnAspSerLysGluAsnPheTrpProLeuIleAla 1510        1520        1530        1540        1550        1560
ACATTATCATGAAGTAATTTCCGGGCGATAAAGACAAGAAGCATCTCAATGGTTTGGG
HisTyrHisGluValIleSerGlyAlaIleLysAspLysLysHisLeuAsnGlyLeuGly 1570        1580        1590        1600        1610        1620
GTTCAACATACAAAGCTTGGTCCAAAGTATGTCAACATTGATAAGTAATGCGTGATCG
PheAsnIleGlnSerLeuValGlnLysTyrValAsnIleAspLysValMetArgAspArg 1630        1640        1650        1660        1670        1680
TGCTCTTGGTAAATCACGTGGGGCACTTGTTGAGCAACGTAGGTATGTTCCACCAATC
AlaLeuGlyLysSerArgGlyGlyThrLeuLeuSerAsnValGlyMetPheHisGlnSer 1690        1700        1710        1720        1730        1740
GGAGGAGACCGAACACAAGTATCGTATAAGAGATTTGGCCTTTGGTCAATTCAAGGGTC
GluGluThrGluHisLysTyrArgIleArgAspLeuAlaPheGlyGlnPheGlyGlySer
```

FIG. 17(f)

```
       1750      1760      1770      1780      1790      1800
ATGGCATCAAGCTTTTTCATTGGGTGTGTTTCTTCGACTAATGTGAAGGGAATGAACATTTT
 TrpHisGlnAlaPheSerLeuGlyValSerSerThrAsnValLysGlyMetAsnIleLeu 1810      1820      1830      1840      1850      1860
GATTCTTCAACGAAAAATGTCTGGGTAGTCAAGAATTGTTGGAGGAACTTTGTGCTAT
 IleSerSerThrLysAsnValValGlySerGlnGluLeuLeuGluLeuLeuCysAlaMet 1870      1880      1890      1900      1910      1920
GTACAAGGCTCTGCTTTAAATCCCTGATTCTTCTTAAGACAATATGATGGTGGATACCTT
 TyrLysAlaLeuLeuLeuAsnPro 1930      1940      1950      1960      1970      1980
TAAAAATTATAGTTTATATTGTAGGGCCTATCCCTGTTTGATATTATAAGTTTTTTTAGCT 1990      2000      2010      2020      2030      2040
TGTAGAGAGAAATGGTATCAGTTTTCTTTTACTAAGATTCGAACTAATCAATATCTCAAAG 2050      2060      2070      2080
TGATTAAACGACGTGTGTAAGTAAGTGTACAGAAA
```

ALCOHOL ACETYLTRANSFERASE GENES AND USE THEREOF

This application is a divisional of application Ser. No. 08/077,939, filed on Jun. 18, 1993 now U.S. Pat. No. 5,521,088.

BACKGROUND OF THE INVENTION

1. Field of the Invention

The present invention relates to an alcohol acetyltransferase ("AATase") produced by, for example, *Saccharomyces cerevisiae*, a DNA sequence encoding, i.e., having an ability for biotechnologically producing, AATase, and a yeast having an improved ester producing ability due to the transformation with the DNA sequence. The present invention also relates to a process for producing an alcoholic beverage having an enhanced ester flavor.

2. Related Art

It is well known that acetate esters affect the flavor quality of alcoholic beverages such as sake, beer, wine and whisky. These esters are in general present in the fermented supernatant, because yeast produces a various kinds of alcohols which are further converted into esters during a fermentation procedure.

In particular, isoamyl acetate is an ester which provides a good fruity flavor for alcoholic beverages. It has been suggested that the ratio of isomyl acetate to isoamyl alcohol, which is a precursor of isomyl acetate, is closely related to the evaluation value of the sensary test. For example, sake having a great ratio of isomyl acetate to isoamyl alcohol valued as "Ginjo-shu" in the sensary test (JOHSHI HOKOKU, No. 145, P. 26 (1973).

As previously reported by Yoshioka et al., Agric. Biol. Chem., 45, 2188 (1981), AATase is an enzyme which plays primary role in the production of isoamyl acetate. The AATase synthesizes isoamyl acetate by the condensation of isoamyl alcohol and acetyl-CoA. Furthermore, AATase has been known to have a wide substrate specificity and to produce many acetate esters such as ethyl acetate in the same mechanism as described above.

Therefore, in order to increase the esters, such as isoamyl acetate in the alcoholic beverages, it is effective to enhance the AATase activity of a yeast. Some of the conventional consideration in the production of the alcoholic beverages, for example, selecting raw materials or controlling fermentation conditions, as a result, have enhanced the activity of the AATase.

However, though it has been well known that AATase is important enzyme for the production of esters, there are few reports referring. to the AATase. Partial purifications of the enzyme have been described in some reports (for example, NIPPON NOGEI KAGAKUKAISHI, 63, 435 (1989); Agric. Biol. Chem., 54, 1485 (1990); NIPPON JOZO KYOKAISHI, 87, 334 (1992), but, because AATase has very labile activity, complete purification of AATase, and the cloning of the gene encoding AATase has not been reported, so far.

SUMMARY OF THE INVENTION

An object of the present invention is to reveal the structure of AATase and isolate the AATase gene, thereby to obtain a transformed yeast having an enhanced AATase producing ability and to produce an alcoholic beverage having an enhanced ester flavor.

According to the first embodiment of the present invention, the present invention provides an AATase originated from yeast having an ability for transferring the acetyl group from acetyl-CoA to an alcohol to produce an acetate ester and having a molecular weight of approximately 60,000 by SDS-PAGE.

According to the second embodiment of the present invention, the present invention provides an AATase comprising a polypeptide selected from a group consisting of:

(1a) a polypeptide having an amino acid .sequence from A to B of the amino acid sequence (SEQ ID NO:15) (SEQ ID NO:19 or residue 19–525 of SEQ ID NO:19) shown in FIG. 1;

(1b) a polypeptide having an amino acid sequence from A to B of the amino acid sequence (SEQ ID NO:17) shown in FIG. 2; and (1c) a polypeptide having an amino acid sequence from A to C or B to C (SEQ ID NO:19 or residue 19–525 of SEQ ID NO:19) of the amino acid sequence shown in FIG. 17.

According to the third embodiment of the present invention, the present invention provides the AATase encoding gene having a DNA sequence selected from a group the consisting of:

(2a) a DNA sequence encoding a polypeptide having an amino acid sequence from A to B of the amino acid sequence (SEQ ID NO:15) shown in FIG. 1;

(2b) a DNA sequence encoding a polypeptide having an amino acid sequence from A to B of the amino acid sequence (SEQ ID NO:17) shown in FIG. 2; and (2c) a DNA sequence encoding a polypeptide having an amino acid sequence from A to C or B to C (SEQ ID NO:19 or residue 19–525 of SEQ ID NO:19) of the amino acid sequence shown in FIG. 17.

According to the fourth embodiment of the present invention, the present invention provides a DNA sequence comprising an AATase gene selected from a group consisting of:

(3a) an AATase gene having a DNA sequence from A to B (bases 233–1808 of SEQ ID NO:14) of the DNA sequence shown in FIG. 1;

(3b) an AATase gene having a DNA sequence from A to B (bases 346–1920 of SEQ ID NO:16) of the DNA sequence shown in FIG. 2;

(3c) an AATase gene having a DNA sequence from A to C or B to C (bases 311–1885 or 365–1885 SEQ ID NO:18) of the DNA sequence shown in FIG. 17; and (3d) a DNA sequence which hybridizes with any one of genes (3a) to (3c).

According to the fifth embodiment of the present invention, the present invention provides a transformed yeast having an enhanced AATase producing ability due to the transformation using the AATase gene selected from (2a) to (2c) or a DNA sequence selected from (3a) to (3d).

According to the sixth embodiment of the present invention, the present invention provides a process for producing a alcoholic beverage having an enriched ester flavor using a transformed yeast as described above.

According to the seventh embodiment of the present invention, the present invention provides a method for isolating a DNA sequence encoding AATase, comprising the steps of:

(a) preparing a DNA fragment having a length of at least 20 bases of a DNA sequence which encodes a polypeptide having an amino acid sequence from A to B (SEQ ID NO:15) of the amino acid sequence shown in FIG. 1;

(b) preparing a gene library which has been made from DNA strands having a substantially same length in the range from 5×10³ to 30×10³ bases obtained by cutting the chromosome of a yeast;

(c) cloning a DNA fragment by hybridization from gene library of (b), using the DNA fragment of (a) as a probe.

The terms "DNA fragment" "DNA sequence" and "gene" are herein intended to be substantially synonymously.

Since the AATase gene have been obtained, a yeast can be transformed using this gene as a foreign gene by a genetic engineering method. That is, the gene can be transfected into a yeast cell as a extranuclear and/or intranuclear gene to afford the yeast an AATase producing ability greater than that of the host cell, and using these transformants an alcoholic beverage having the enriched ester flavor can be made.

BRIEF DESCRIPTION OF THE DRAWINGS

FIGS. 1(a) and (b) show an amino acid sequence (SEQ ID NO:15) of AATase and DNA sequence (SEQ ID NO:14) of the AATase encoding gene according to the present invention;

FIGS. 2(a) and (b) show a amino acid sequence (SEQ ID NO:17) of AATase and DNA sequence (SEQ ID NO:16) of another AATase encoding gene according to the present invention;

FIG. 3 shows a restriction map of the AATase encoding gene originated from a sake yeast according to the present invention;

FIG. 15 shows a restriction map of the brewery lager yeast vector YATL1G having the AATase 1 gene originated from a brewery lager yeast according to the present invention;

FIGS. 17(a)–(f) shows the amino acids (SEQ ID NO:19) and DNA sequence (SEQ ID NO:19) of the brewery lager yeast AATase 2 gene according to the present invention.

DETAILED DESCRIPTION OF THE INVENTION

AATase

Figure 4:
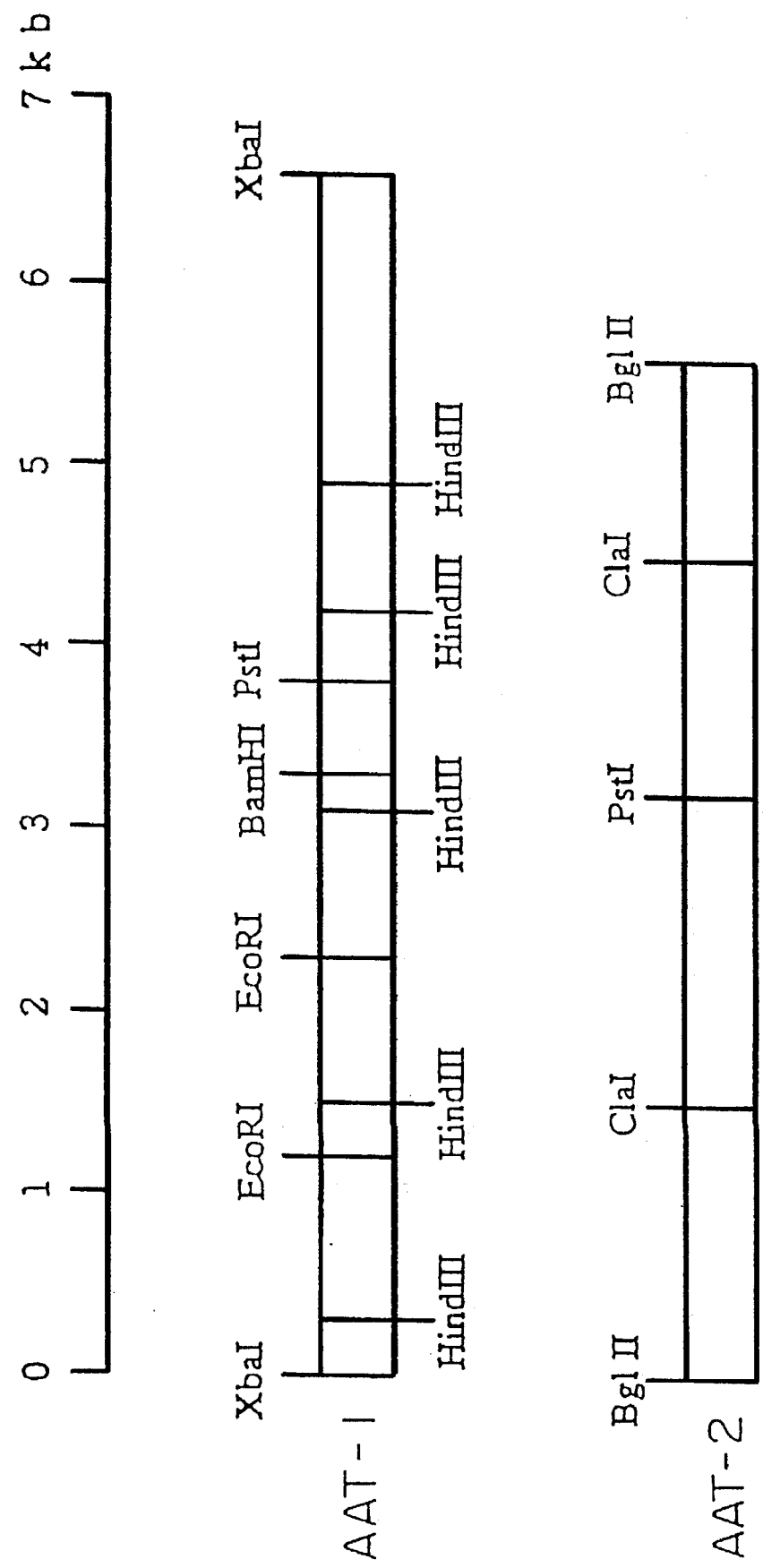
FIG. 4 shows two restriction maps of the AATase originated from a brewery lager yeast according to the present invention.

AATase, alcohol acetyltransferase, is an enzyme having an ability for producing an acetate ester by transferring the acetyl group from acetyl-CoA to alcohols.

The alcohols herein primarily mean alcohols having straight or branched chains having 1 to 6 carbon atoms. According to our studies, however, it has been found that the AATase may employ as substrates alcohols having a higher number of carbon atoms such as 2-phenyl ethylalcohol.

Thus, "the alcohols" should be construed to include a wide range of alcohols, if it is necessary to discuss the substrate alcohol of the AATase in the present invention.

The AATase according to the present invention is originated from yeast. The AATase is specifically obtained from Saccharomyces cerevisiae and is a polypeptide having any one of the polypeptides (1a)–(1c) defined above. Specifically, the polypeptide includes a polypeptide having an amino acid sequence from A to B (SEQ ID NO:15) of the amino acid sequence shown in FIG. 1; a polypeptide having an amino acid sequence from A to B (SEQ ID NO:17) of the amino acid sequence shown in FIG. 2; a polypeptide having an amino acid sequence from A to C (SEQ ID NO:19) of the amino acid sequence shown in FIG. 17; and a polypeptide having an amino acid sequence from B to C (residues 19–525 of SEQ ID NO:19) of the amino acid sequence shown in FIG. 17. Furthermore, it has been clarified by genetic engineering for protein engineering that the physiological activity of a polypeptide may be maintained with the addition, insertion, elimination, deletion or substitution of one or more of the amino acids of the polypeptide. The polypeptide therefore include a modified polypeptide of any one of the above polypeptides due to the addition, insertion, elimination, deletion or substitution of one or more of amino acid of the polypeptide so long as the modified polypeptide has an AATase activity.

Saccharomyces cerevisiae used herein is a microorganism described in "The yeast, a taxonomic study", the 3rd Edition, (ed. by N. J. W. Kreger-van Rij, Elsevier Publishers B. V., Amsterdam (1984), page 379), or a synonym or mutant thereof.

AATase and its purification method have been reported in some papers, for instance, NIPPON NOGEIKAGAKU KAISHI, 63, 435 (1989); Agric. Biol. Chem., 54, 1485 (1990); NIPPON JOSO KYOKAISHI, 87, 334 (1992). However, so far as the present inventors know, the AATase has not been purified to homogeneity, so its amino acid sequence has not been determined.

The present inventors have now found that an affinity column with 1-hexanol as a ligand can be used successfully for purifying the AATase. We have thus completely purified the AATase from Saccharomyces cerevisiae by use of this affinity column and defined some properties of the enzyme. The amino acid sequence shown in FIG. 1 (SEQ ID NO:15) is obtained by analysis of the AATase originated from Saccharomyces cerevisiae which has thus purified to homogenity.

The typical property of the AATase which have been defined according to the present invention includes the molecular weight of the AATase. Although the molecular weight of the AATase previously reported is in the range from 45,000 to 56,000, the molecular weight of the AATase purified according to the present invention is approximately 60,000 by SDS-polyacrylamide gel electrophoresis (SDS-PAGE), suggesting that it is different from the protein reported previously. The molecular weight of the AATase deduced from the DNA sequence was ca. 61,000.

The AATase of the present invention has enzymological and physicochemical properties as set forth below.

(a) Action:

This enzyme acts on a variety of alcohol such as ethyl alcohol and acetyl-CoA to produce an acetate ester.

(b) Substrate specificity:

This enzyme acts on various kinds of alcohol having 2 to 5 carbon atoms, more efficiently on alcohols having 2 to 5 carbon atoms. In addition, the enzyme acts more efficiently on straight chain alcohols rather branched chain alcohols.

(c) Molecular weight: ca. 60,000

(d) Optimum and stable pH:

optimum pH: 8.0, stable pH: 7.5–8.5

(e) Optimum and stable temperature:

optimum temperature: 25° C., stable temperature: 4° C.;

(f) Inhibitors:

This enzyme is intensively inhibited by parachloromercury benzoate (PCMB) and dithiobisbenzoic acid (DTNB);

(g) Effects of various fatty acids on the activity:

This enzyme is not noticeably inhibited by a saturated fatty acid but intensively inhibited by an unsaturated fatty acid;

(h) Km value to isoamyl alcohol and acetyl-CoA:

isoamyl alcohol: 29.8 mM, acetyl CoA: 190 µM.

The AATase can be obtained by a procedure comprising culturing yeast cells of $Saccharomyces\ cerevisiae$ KYOKAI No. 7 and recovering and purifying the crude enzyme from the content of the organism as described in Examples below. DNA sequence or DNA fragment/gene which produces AATase In the present invention, the DNA sequence or DNA fragment having an ability of producing AATase means the DNA sequence or DNA fragment which codes for a polypeptide having AATase activities. The amino acid sequence of a polypeptide encoded by the sequence or fragment, i.e., the AATase, is selected from the group consisting of the following (2a)–(2c), and is specifically selected from the group consisting of the following (3a)–(3d):

(2a) a DNA sequence encoding a polypeptide having an amino acid sequence from A to B (SEQ ID NO:15) of the amino acid sequence shown in FIG. 1;

(2b) a DNA sequence encoding a polypeptide having an amino acid sequence from A to B (SEQ ID NO:17) of the amino acid sequence shown in FIG. 2;

(2c) a DNA sequence encoding a polypeptide having an amino acid sequence from A to C or B to C (SEQ ID NO:19 or residues 19–525 of SEQ ID NO:19) of the amino acid sequence shown in FIG. 17.

(3a) an AATase gene having a DNA sequence from A to B (bases 233–1808 of SEQ ID NO:14) of the DNA sequence shown in FIG. 1;

(3b) an AATase gene having a DNA sequence from A to B (bases 346–1920 of SEQ ID NO:16) of the DNA sequence shown in FIG. 2;

(3c) an AATase gene having a DNA sequence from A to C or B to C (bases 311–1885 of SEQ ID NO:18) of the DNA sequence shown in FIG. 17; and (3d) a DNA sequence capable of hybridizing with any one of genes (3a) to (3c).

The DNA sequence varies depending upon the variation of the polypeptide. In addition, it is well known by one skilled in the art that a DNA sequence is easily defined according to the knowledge referring to the so called "degeneracy", once an amino acid sequence is given. Thus, one skilled in the art can understand that certain codons present in the sequence shown in FIGS. 1, 2 and 17 can be substituted by other codons and produce a same polypeptide. This means that the DNA sequence (or DNA fragment) of the present invention includes DNA sequences which encode the same peptide but are different DNA sequences in which codons in the degeneracy relation are used. Furthermore, one skilled in the art can understand that the DNA sequence of the present invention include the DNA sequence which encodes a modified polypeptide oK any of one of the polypeptides (1a) to (1c) due to the addition, insertion, elimination, deletion or substitution of one or more amino acid of these polypeptides. In this connection, the term "encoding" is synonymous with the term "capable of encoding".

The DNA sequence of the present invention may be obtained from a natural gene source or obtained by total synthesis or semi-synthesis (i.e., synthesized with use of a part of a DNA sequence originated from a natural gene source).

Form the natural gene source, the DNA sequence of the present invention can be obtained by conducting DNA manipulations such as plaque hybridization, colony hybridization and PCR process using a probe which is a part of a DNA sequence producing the AATase of the present invention. These methods are well-known to one skilled in the art and can be easily performed.

Suitable gene sources for obtaining a DNA sequence having an AATase producing ability by these methods include for example bacteria, yeast and plants. Among these gene sources, yeast which is currently used for the production of fermentation foods such as sake and soy sauce is one of the best candidate having a DNA sequence of the present invention.

The typical form of the DNA sequence of the present invention is a polypeptide which has a length just corresponding to the length of AATase. In addition, the DNA sequence of the present invention may have an additional DNA sequences which are bonded upstream and/or downstream the sequence. A specific example of the latter is a vector such as plasmid carrying the DNA sequence of the present invention.

Suitable example of the DNA sequence of the present invention is from A to B of the amino acid sequence shown in FIG. 1. (bases 233–1808 of SEQ ID NO:14) This sequence is obtained by analyzing an AATase encoding gene obtained from a yeast strain, SAKE YEAST KYOKAI No. 7.

Transformation

The procedure or method for obtaining a transformant is commonly used in the field of genetic engineering. In addition to the method described below, any conventional transformation method (for example, Analytical Biochemistry, 163, 391 (1987)), is useful to obtain the transformant.

Vectors which can be used include all of the known vectors for yeast such as YRp vectors (multicopy vectors for yeast containing the ARS sequence of the yeast chromosome as a replication origin), YEp vectors (multicopy vectors for yeast containing the replication origin of the 2 μm DNA of yeast), YCp vectors (single copy vectors for yeast containing the DNA sequence of the ARS sequence of the gene chromosome. and the DNA sequence of the centromere of the yeast chromosome), YIp vectors (integrating vectors for yeast having no replication origin of the yeast). These vectors is well-known and described in "Genetic Engineering for the Production of Materials", NIPPON NOGEI KAGAKUKAI ABC Series, ASAKURA SHOTEN, p. 68, but also can be easily prepared.

In addition, in order to express the gene of the DNA sequence according to the present invention or to increase or decrease the expression, it is preferable that the expression vector contains a promoter which is a unit for controlling transcription and translation in the 5'-upstream region and a terminator in the 3'-downstream region of the DNA sequence. Suitable promoters and terminators are for example those originated from the AATase gene itself, those originated from any known genes such as alcohol dehydrogenase gene (J. Biol. Chem., 257, 3018 (1982)), phosphoglycerate kinase gene (Nucleic Acids Res., 10, 7791 (1982)) or glycerolaldehyde-3-phosphate dehydrogenase gene [J. Biol. Chem., 254, 9839 (1979)) or those which are the artificial modifications of the former.

The yeast to be transformed in the present invention, i.e. the host yeast, may be any yeast strain which belongs taxonomically to the category of yeast, but for the purpose of the present invention, a yeast strain for producing alcoholic beverages which belongs to *Saccharomyces cerevisiae* such as brewery yeast, sake yeast and wine yeast are preferred. Suitable examples of yeast include brewery yeast such as ATCC 26292, ATCC 2704, ATCC 32634 and AJL 2155; sake yeast such as ATCC 4134, ATCC 26421 and IFO 2347; and wine yeast such as ATCC 38637, ATCC 38638 and IFO 2260.

Another group preferred as the host yeast is baker's yeast such as ATCC 32120.

Preparation of Alcoholic Beverages

The transformed yeast having an enhanced AATase producing ability is provided with a character intrinsic to the host yeast as well as the introduced character. The transformant thus can be used for various applications focussed to the intrinsic character.

If the host yeast is a yeast for preparing alcoholic beverages, the transformed yeast also has an ability for fermenting saccharides to alcohols. Therefore, the transformed yeast according to the present invention provides an alcoholic beverages having an enhanced or enriched ester flavor.

Typical alcoholic beverages include sake, wine, whiskey and beer. In addition, the process for preparing these alcoholic beverages are well-known.

Production of Other AATases

As described above, the present invention provides the AATase gene encoding amino acid sequence from A to B of the amino acid sequence shown in FIG. 1. (SEQ ID NO:15) According to another aspect of the present invention, the present invention provides other AATase genes. It has now been found that a different kind of AATase producing gene is obtained from a least gene library by use of a probe which is a relatively short DNA fragment of a DNA sequence encoding the amino acid sequence from A to B (SEQ ID NO:15) of the amino acid sequence shown in FIG. 1. It is interesting in this case that the probe originated from the DNA sequence obtained from a "sake" yeast provided two different DNA sequences having an AATase producing ability from the gene library of a brewery lager yeast. In addition, while both of these DNA sequences are capable of producing AATase, the restriction maps, DNA sequences and the amino acid sequences of the DNA sequences are different from those of the amino acid sequence shown in FIG. 1 (SEQ ID NO:15) originated from a sake yeast.

In the process of isolating these DNA sequences, a DNA fragment as a probe is first provided. The probe has preferably a length of at least 20 bases of the DNA sequence encoding a polypeptide having an amino acid from A to B (SEQ ID NO:15) of the amino acid sequence substantially shown in FIG. 1.

The length of the DNA strand as the probe is preferably at least 20 bases, since sufficient hybridization will not occur with an excessively short probe. The DNA strand has more preferably a length of 100 bases or more.

The gene library to which the probe is applied preferably comprises vectors containing DNA fragments having a substantially same length in the range from $5 \times 10^3$ bases to $30 \times 10^3$ bases obtained by cutting a chromosome of yeast by chemical or physical means such as restriction enzyme or supersonic.

The restriction enzyme to be used in this procedure, of which the kinds and/or the reaction conditions should be set up so that for a certain yeast chromosome the DNA strands having a length within the above range are obtained. In case of making gene library from brewery yeast chromosommal DNA, suitable restriction enzymes include for example Sau3AI or MboI.

It is desirable that the DNA fragment obtained by cutting have substantially the same length in the range from $5 \times 10^3$ bases to $30 \times 10^3$ bases, in other words, the DNA fragment in the digested product with restriction enzyme has uniform length within the range from $5 \times 10^3$ bases to $30 \times 10^3$ bases.

Cloning of the complementary DNA strands from the gene library using probes, and the subcloning of this cloned DNA fragments, for example, into the yeast is easily performed according to the well-known genetic engineering method (for example, Molecular Cloning, Cold Spring Harbor Laboratory (1988)).

The amino acid sequence shown in FIG. 2 (SEQ ID NO:17) is a polypeptide encoded by one of the two DNA sequences obtained from the brewery lager yeast gene library by using a probe which has a sequence corresponding to the DNA sequence from 234 to 1451 shown in FIG. 1 (SEQ ID NO:14). It is apparent from comparing the figures, the AATases originated from brewery lager yeast and sake yeast, are different from each other only in 12 base pairs and 3 amino acids. The polypeptide having an amino acid sequence from A to B shown in FIG. 2 (SEQ ID NO:17) which was obtained with the hybridization/cloning method described above, can also be regarded as an equivalent polypeptide of the amino acid sequence from A to B (SEQ ID NO:15) shown in FIG. 1, i.e., as a modified polypeptide in which some of amino acids have been deleted, substituted or added.

Similarly, the amino acid sequences (from A to C or from B to C) shown in FIG. 17 (SEQ ID NO:19 or residues 19–525 of SEQ ID NO:19) is polypeptides encoded by the other DNA sequence obtained from the gene library of brewery larger yeast by using the some probe. It is apparent from comparing the figures, this AATase originated from brewery lager yeast is different from the AATase originated from sake yeast in 332 base pairs and 102 amino acids.

EXAMPLES

The following examples are offered by way of illustration and are not intended to limit the invention any way. In the Examples, all percentages are by weight unless otherwise mentioned.

(1) Preparation of AATase

The enzyme of the present invention can be obtained from the culture of an microoprganism which is a member of Saccharomyces and produces an enzyme having the aforementioned properties. The preferred preparation process is as follows:

(1)-(i) Assay of AATase activity

A 1 ml of a solution containing a buffer for AATase reaction (25 mM imidazole hydrochloride buffer (pH 7.5 mM), 1 mM acetyl-CoA, 0.1% Triton X-100, 0.5% isoamyl alcohol, 1 mM dithiothreitol, 0.1M sodium chloride, 20% glycerol: or 10 mM phosphate buffer (pH 7.5 mM), 1 mM acetyl-CoA, 0.1% Triton X-100, 0.5% isoamyl alcohol, 1 mM dithiothreitol, 0.1M sodium chloride, 20% glycerol) and the enzyme of the present invention was encapsulated into a 20 ml vial and reacted at 25° C. for 1 hour. After incubation, the vial was opened and the reaction was stopped by adding 0.6 g of sodium chloride. n-Butanol was added as an internal standard to the reaction mixture up to 50 ppm. The vial was capped with a teflon stopper. Then, the isoamyl acetate generated was determined with the head space gas chromatography (Shimadzu GC-9A, HSS-2A). under the following condition:

Column: glass column 2.1 m×3 mm

Stationary phase: 10% Polyethylene Glycol 1540 Diasolid L (60/80 mesh)

Column temperature: 75° C.

Injection temperature: 150° C.

Carrier gas: nitrogen

Flow rate: 50 ml/min

Sample volume: 0.8 ml.

(1)-(ii) Preparation of crude enzyme

Yeast cells of KYOKAI No. 7 were inoculated in 500 ml of a YPD culture (1% yeast extract, 2% bactopeptone, glucose) and cultured at 15° C. for 3 days. A 25 ml of the culture solution was inoculated into 1000 ml of a YPD culture medium in 20 set of Erlenmeyer flasks having a 200 ml volume and cultured at 30° C. for 12 hours. Cells were then collected by centrifugation (3,000 rpm, 10 min) and suspended into a buffer (50 mM Tris hydrochloride buffer (pH 7.5 mM), 0.1M sodium sulfite, 0.8M potassium chloride) having a volume 10 times that of the cells. After this, "ZYMOLYASE 100T" (yeast cell cleaving enzyme commercially available from SEIKAGAKU KOGYO K.K.; Japanese Patent No. 702095, U.S. Pat. No. 3,917,510) was added in an amount of 1/1,000 to the weight of the cells. The mixture was incubated with shaking at 30° C. for 1 hour. Then, the resulting protoplast was collected by centrifugation at 3,000 rpm for 5 minutes, suspended in 400 ml of a buffer for the disruption of cells (25 mM imidazole hydrochloride buffer (pH 7.5 mM), 0.6M potassium chloride, 1 mM sodium ethylenediaminetetraacetate (EDTA)) and disrupted with a microbe cell disrupting apparatus "POLYTRON PT10" (KINEMATICA Co.). The cell debris were removed by centrifugation at 45,000 rpm to give a crude enzyme solution.

(1)-(iii) Preparation of microsome fraction

After the crude enzyme solution obtained in (1)-(ii) was centrifuged at 100,000×G for 2 hours, and the resulting precipitate ("microsomal fraction") was suspended in 40 ml of a buffer (25 mM imidazole hydrochloride buffer (pH 7.5 mM), 1 mM dithiothreitol). When the suspension was not immediately used, it was stored at -20° C.

(1)-(iv) Preparation of solubilized enzyme

After the microsomal fraction obtained in (1)-(iii) was placed in a Erlenmeyer flask, Triton X-100 was added in an amount of 1/100 of the volume. The mixture was gently agitated with a magnetic stirrer at 4° C. for 60 minutes so that the mixture was not foamed. The mixture was then centrifuged at 100,000×G for 2 hours. The supernatant was then dialyzed overnight against the buffer A (25 mM imidazole hydrochloride buffer (pH 7.2), 0.1% Triton X-100, 0.5% isoamyl alcohol, 1 mM dithiothreitol, 20% glycerol).

(1)-(v) Purification of enzyme

By repeating the procedures (1)-(ii) and (1)-(iii) twenty times, microsomal fraction was obtained and stored at -20° C. Then by subjecting the procedure (1)-(iv) to the microsomal fraction, the solubilized enzyme fraction for further purification was obtained. The solubilized enzyme fraction was first applied to a POLYBUFFER EXCHANGER 94 column (Pharmacia) (adsorption: buffer A; elution: buffer A+a gradient of 0.0 to 0.6M sodium chloride).

The active fraction was collected and repeatedly applied to the POLYBUFFER EXCHANGER 94 column.

The active fraction was further purified in the manner as shown in Table 1. That is, the active fraction was purified by (1) ion-exchange column chromatography with DEAE Toyopearl 55 (TOSOH, adsorption: buffer A; elution: buffer A+a gradient of 0.0 to 0.2M sodium chloride);

(2) gel filtration chromatography with Toyopearl HW60 (TOSOH) using buffer B (10 mM phosphate buffer. (pH 7.5 mM), 0.1% Triton X-100, 0.5% isoamyl alcohol, 1 mM dithiothreitol, 0.1M sodium chloride, 20% glycerol);

(3) hydroxyapatite column chromatography (Wako Pure Chemical Industries, Ltd., adsorption: buffer B; elution: buffer B+a gradient of 10 to 50 mM phosphate buffer (pH 7.5 mM); or (4) octyl sepharose column chromatography (Pharmacia, adsorption: 50 mM imidazole hydrochloride (pH 7.5 mM), 0.5% isoamyl alcohol, 1 mM dithiothreitol, 0.1M sodium chloride, 20% glycerol; solution: 50 mM imidazole hydrochloride (pH 7.5 mM), 0.1% Triton X-100, 0.5% isoamyl alcohol, 1 mM dithiothreitol, 0.1M sodium chloride, 20% glycerol).

As shown in Table 1, AATase was purified approximately 2,000 times on the basis of the specific activity. However, a small amount of other proteins was still observed in SDS-PAGE with silver stain, thus indicating insufficient purification.

Figure 8:
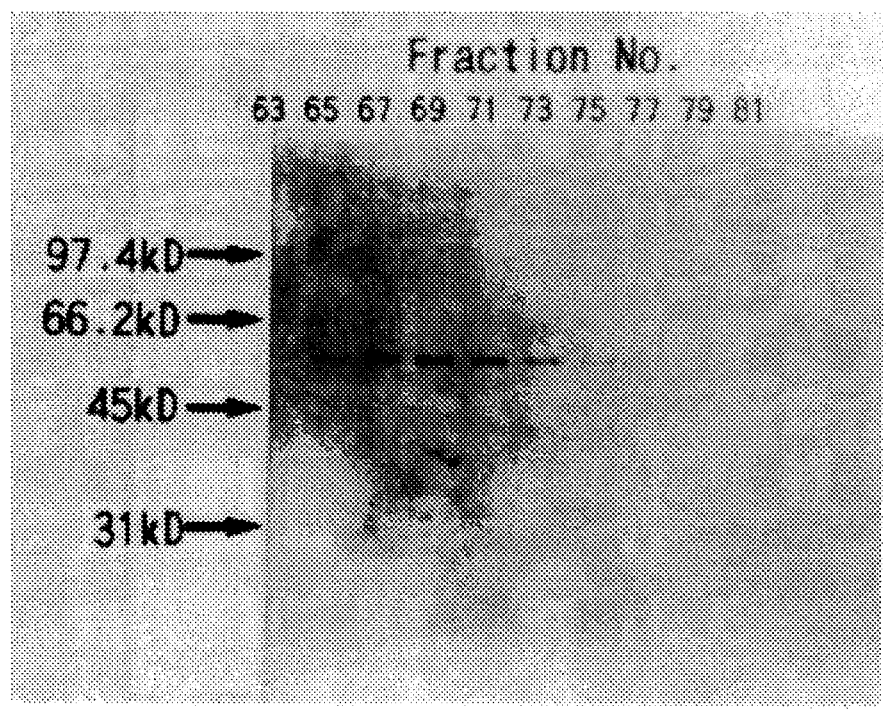
FIG. 8 shows an SDS-polyacrylamide electrophoresis of the AATase active fraction eluted by the affinity chromatography according to the present invention.
Figure 9:
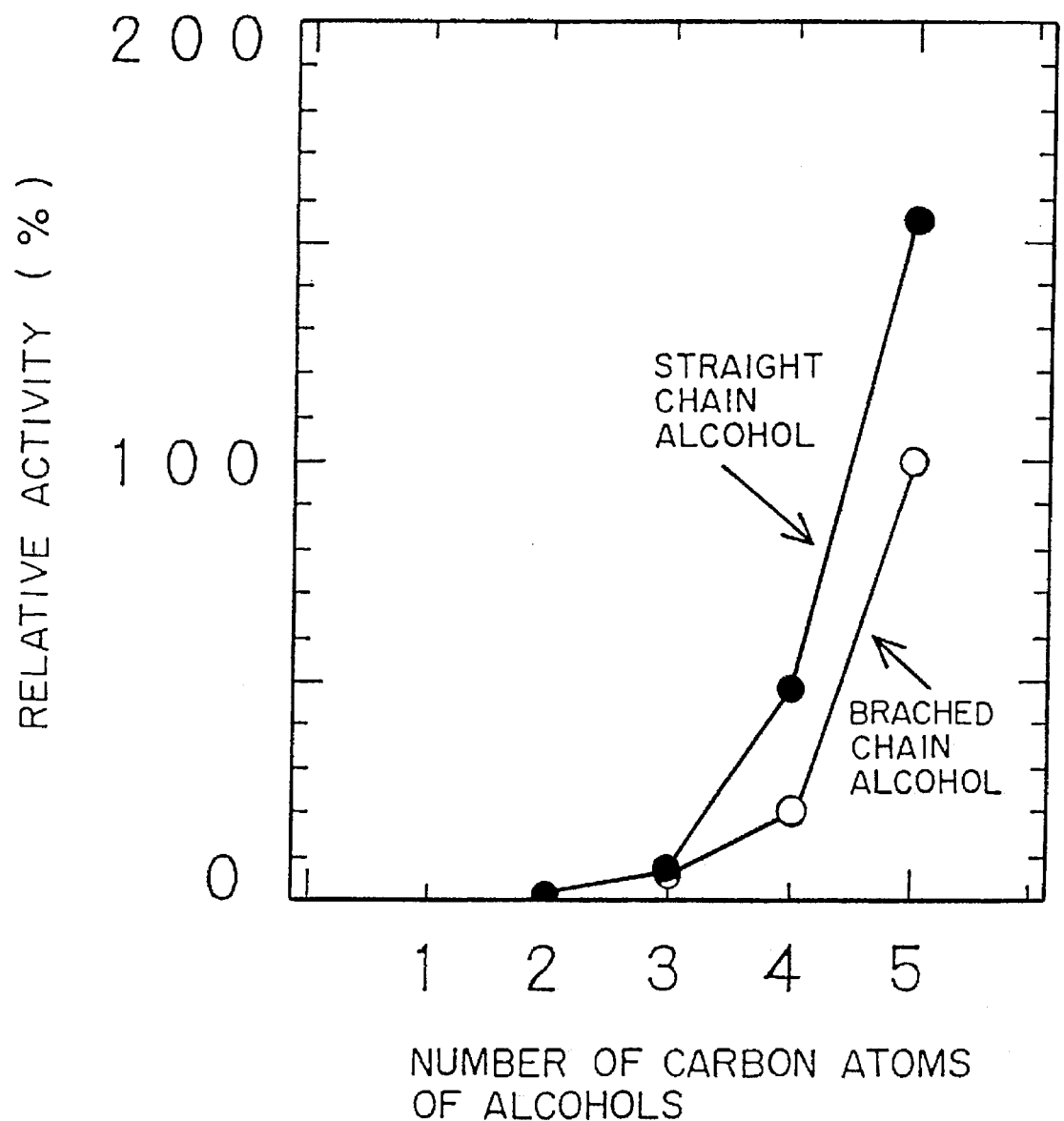
FIG. 9 shows the substrate specificity of the AATase according to the present invention to a variety of alcohols.
Figure 10:
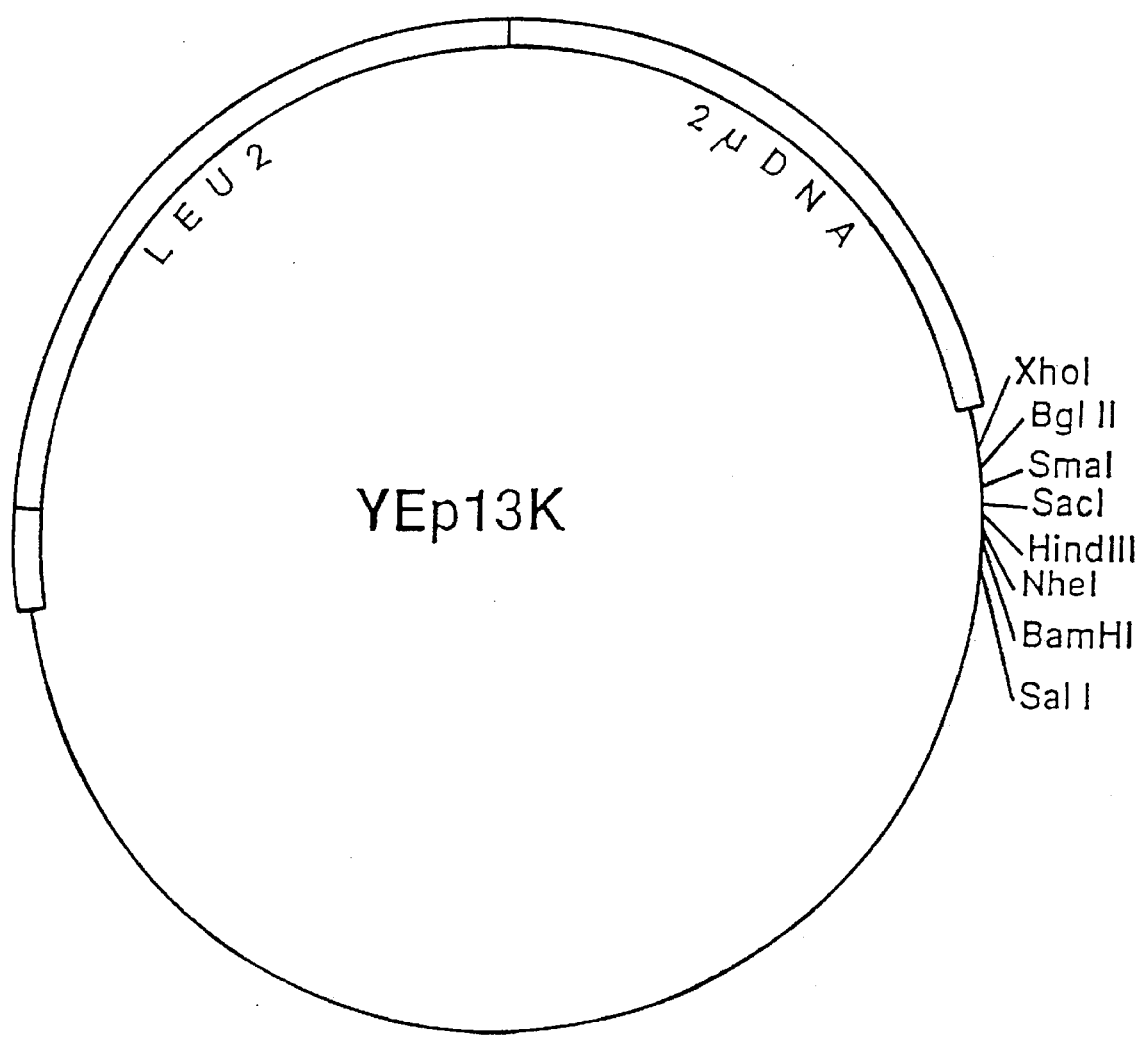
FIG. 10 shows a restriction map of the expression vector YEp13K for yeast.

Thus, the present inventors have carried out affinity chromatography based on the specific affinity between 1-hexanol and AATase. Hexanol Sepharose 4B column was prepared with 6-amino-1-hexanol (Wako Pure Chemical Industries, Ltd.) and CNBr activated Sepharose 4B (Pharmacia) as a support according to the protocol by Pharmacia. Affinity chromatography was conducted with the column (adsorption: 5 mM phosphate buffer (pH 7.2), 0.1% Triton X-100, 20% glycerol, 1 mM dithiothreitol; elution: sodium chloride with a gradient from 0.0 to 0.2M). The active fraction thus obtained as shown in FIG. 9 was subjected to SDS-PAGE and stained wAATase was success. AATase was successfully purified to homogenity since the active fraction was an enzyme which afforded a single band as shown in FIG. 8.

TABLE 1

| Purification of AATase | | | |
| --- | --- | --- | --- |
| | Volume (ml) | Activity (ppm/ml) | Total activity (ppm) |
| Solubilized enzyme | 505 | 119 | 60100 |
| PBE 94 1st. | 395 | 77 | 30400 |
| PBE 94 2nd | 86 | 304 | 26100 |
| DEAE Toyopearl | 24 | 580 | 13900 |
| Toyopearl HW60 | 24 | 708 | 17000 |
| Hydroxy apatite | 7.6 | 1020 | 7750 |

TABLE 1-continued

Purification of AATase

| | | | |
|---|---|---|---|
| Octyl sepharose | 1.0 | 2390 | 2390 |

| | Protein (mg/ml) | Specific activity (ppm/mg protein) | Yield (%) | Rate of Purification |
|---|---|---|---|---|
| Solubilized enzyme | 5.43 | 22 | 100 | 1 |
| PBE 94 1st. | 0.515 | 150 | 51 | 7 |
| PBE 94 2nd. | 1.086 | 280 | 43 | 13 |
| DEAE Toyopearl | 0.96 | 604 | 23 | 27 |
| Toyopearl HW60 | 0.262 | 2700 | 28 | 123 |
| Hydroxy apatite | 0.119 | 8570 | 13 | 266 |
| Octyl sepharose | 0.056 | 42700 | 4 | 1940 |

(2) Properties of AATase
(2)-(i) Substrate specificity

According to studies of substrate specificity of AATase to various kinds of alcohol by using the aforementioned analytical apparatuses and methods, AATase acts on a variety of alcohol having 1–5 carbon atoms. AATase acts more efficiently on alcohols having higher number of carbon atoms. In addition, AATase acts more efficiently on straight chain alcohols rather than branched chain alcohols (FIG. 9).

(2)-(ii) Optimum pH and pH stability

In order to examine the effect of pH on the stability of the enzyme, the enzyme was maintained at respective pH of from pH 5 to 9 (pH 5–6:50 mM citrate-phosphate buffer; pH 6–8: 50 mM phosphate buffer; pH 8–9: 50 mM Tris-phosphate buffer) under the condition of 4° C. for 22 hours. The enzyme activity was assayed at pH 7.5 mM with 0.2M disodium phosphate according to the method (1)-(i).

In order to evaluate the effect of pH on the activity of the enzyme, the enzyme activities were assayed at respective pH of from 5 to 9 (pH 5–6:50 mM citrate-phosphate buffer; pH 6–8: 50 mM phosphate buffer; pH 8–9: 50 mM Tris-phosphate buffer) according to the method (1)-(i).

The enzyme of the present invention was stable within the pH range from 7.5 mM to 8.5. The optimum pH was 8.0.

(2)-(iii) Optimum temperature and thermal stability

In order to examine the effect of temperature on the activity of the enzyme, the enzyme activities were assayed at various temperatures according to the method of (1)-(i).

In addition, after the enzyme incubated at each temperature for 30 minutes, the enzyme activities were assayed according to the method of (1)-(i).

The optimum temperature was 25° C. The enzyme was stable at 4° C., but it was very unstable at a temperature of higher than 4° C..

(2)-(iv) Inhibition

For the examination of effects of various inhibitors on the enzyme activity, enzyme assay was carried out in a reaction buffer described in (1)-(i) containing inhibitors (1 mM) shown in Table 2 according to the method of (1)-(i). The results are shown in Table 2. The enzyme according to the present invention is believed to be an SH enzyme, because it was inhibited strongly by p-chloromercuribenzoic acid (PCMB) and dithiobis (2-nitrobenzoic acid) (DTNB).

TABLE 2

| Inhibitor (1 mM) | Relative activity (%) | Inhibitor (1 mM) | Relative activity (%) |
|---|---|---|---|
| None | 100 | $ZnCl_2$ | 12.7 |
| KCl | 98.6 | $MnCl_2$ | 53.3 |
| $MgCl_2$ | 86.2 | $HgCl_2$ | 0 |
| $CaCl_2$ | 87.7 | $SnCl_2$ | 52.0 |
| $BaCl_2$ | 73.7 | TNBS* | 16.8 |
| $FeCl_3$ | 54.5 | PCMB* | 0 |
| $CoCl_2$ | 37.6 | DTNB* | 0 |
| $CdCl_2$ | 3.1 | PMSF* | 70.2 |
| $NiCl_3$ | 22.3 | 1,10-phenanthroline | 87.9 |
| $CuSO_4$ | 0 | | |

*1 mM TNBS: Trinitrobenzenesulfonic acid,
0.1 mM PCMB: p-Chloromercuribenzoic acid
0.1 mM DTNB: Dithiobis(2-nitrobenzoic acid)
1 mM PMSF: Phenylmethanesulfonyl fluoride.

(2)-(v) Effects of fatty acids on enzyme activity

Various fatty acids were added in an amount of 2 mM to the reaction buffer of (1)-(i) to examine the effect of the fatty acids on the enzyme activity. The activity was assayed according to the method (1)-(i). The results are shown in Table 3.

TABLE 3

Influence of fatty acids on the enzyme activity

| Fatty acid (2 mM) | | Relative activity (%) |
|---|---|---|
| None | | 100 |
| Myristic acid | $C_{14}H_{28}O_2$ | 60.5 |
| Palmitic acid | $C_{16}H_{32}O_2$ | 88.1 |
| Palmitoleic acid | $C_{16}H_{30}O_2$ | 16.7 |
| Stearic acid | $C_{18}H_{36}O_2$ | 80.5 |
| Oleic acid | $C_{18}H_{34}O_2$ | 59.6 |
| Linoleic acid | $C_{18}H_{32}O_2$ | 4.3 |
| Linolenic acid | $C_{18}H_{30}O_2$ | 32.0 |

(3) Sequencing of partial amino acid sequence

Partial amino acid sequence was determined according to the method described by Iwamatsu (SEIKAGAKU, 63, 139 (1991)) using a polyvinylidene difluoride (PVDF) membrane. The AATase prepared in (1)-(v) was dialyzed against 3 liter of 10 mM formic acid for 1 hour and then lyophilized. The lyophilized enzyme was suspended in a buffer for electrophoresis (10% glycerol, 2.5% SDS, 2% 2-mercaptoethanol, 62 mM Tris hydrochloride buffer (pH 6.8)) and subjected to SDS-PAGE. Then, the enzyme was electroblotted onto a PVDF membrane of 10 cm×7 cm ("ProBlot", Applied Biosystems) using ZARTBLOT IIs model (ZARTRIUS Co.). The electroblotting was carried out at 160 mA for 1 hour according to "Pretreatment method of a sample in PROTEIN SEQUENCER (1)" edited by SHIMAZDU SEISAKUSHO.

PVDF-immobilized enzyme was then cut off and dipped into about 300 μl of a buffer for reduction (6M guanidine hydrochloride-0.5M Tris hydrochloride buffer (pH 3.5), 0.3% EDTA, 2% acetonitrile) with 1 mg of dithiothreitol (DTT) and reduced under argon at 60° C. for about 1 hour. A solution of 2.4 mg of monoiodoacetic acid in 10 μl of 0.5N sodium hydroxide was added. The mixture was then stirred in darkness for 20 minutes. After the PVDF membrane was taken out and washed sufficiently with 2% acetonitrile, the membrane was further stirred in 0.1% SDS for 5 minutes. The PVDF membrane was next rinsed lightly with water, dipped into 0.5% polyvinylpyrrolidone –40 –100 mM acetic acid and left standing for 30 minutes. The PVDF membrane was washed thoroughly with water and cut into square chips having a side of about 1 mm. The chips were dipped into a digestion buffer (8% acetonitrile, 90 mM Tris hydrochloride buffer (pH 9.0)) and digested at room temperature for 15 hours after 1 pmol of ACROMOBACTER PROTEASE I (Wako Pure Chemical Industries, Ltd.) was added. The digested products was separated by reverse phase high performance liquid chromatography (model L6200, HITACHI) with a C8 column (NIPPON MILIPORE, LTD; μ-Bondasphere 5C8, 300A, 2.1×150 mm) to give a dozen or so peptide fragments. The elution of the peptide was carried using the solvent A (0.05% trifluoroacetic acid) with a linear gradient from 2 to 50% of the solvent B (2-propanol/acetonitrile (7:3) containing 0.02% trifluoroacetic acid) at a flow rate of 0.25 ml/min. The amino acid sequencing of the peptide fragments thus was conducted by the automatic Edman degradation method with a vapor phase protein sequencer model 470 (Applied Biosystems) according to manufacturer's instructions.

As a result, the following amino acid sequences were determined:

gradient solution was fractionated in every sampling tube. A portion. of each fraction was subjected to agarose gel electrophoresis to confirm the molecular weight of the chromosomal DNA. Then, the 15–20 kb DNA was collected and recovered by ethanol precipitation.

The digested chromosomal DNA (1 μg) and the λ-EMBL3 vector (1 μg) of a λ-EMBL3/BamH1 vector kit (manufactured by STRATAGENE, purchased from FUNAKOSHI) were ligated at 16° C. overnight. The ligation product was packaged using a GIGAPACK GOLD (manufactured by STRATAGENE, purchased from FUNAKOSHI). The ligation and packaging were conducted according to manufacturer's instructions. The host strain P2392 of the λ-EMBL3 vector kit was infected with a 50 μl of the packaged solution. One inoculation loop amount of P2392 was cultured in 5 ml of a TB culture medium (1% bactotriptone (DIFCO), 0.5% sodium chloride, 0.2% maltose, pH 7.4) at 37° C. overnight. Then, 1 ml of the culture was inoculated into 50 ml of a TB culture medium

| peak | 1 | | Lys | Trp | Lys | | | | | | | | |
|---|---|---|---|---|---|---|---|---|---|---|---|---|---|
| peak | 2 | (SEQ ID NO: 1) | Lys | Tyr | Val | Asn | Ile | Asp | | | | | |
| peak | 3 | (SEQ ID NO: 2) | Lys | Asn | Gln | Ala | Pro | Val | Gln | Gln | Glu | Cys | Leu |
| peak | 4 | (SEQ ID NO: 3) | Lys | Gly | Met | Asn | Ile | Val | Val | Ala | Ser | | |
| peak | 5 | (SEQ ID NO: 4) | Lys | Tyr | Glu | Glu | Asp | Tyr | Gln | Leu | Leu | Arg | Lys |
| peak | 6 | (SEQ ID NO: 5) | Lys | Gln | Ile | Leu | Glu | Glu | Phe | Lys | | | |
| Peak | 7 | (SEQ ID NO: 6) | Lys | Leu | Asp | Tyr | Ile | Phe | Lys | | | | |
| Peak | 8 | (SEQ ID NO: 7) | Lys | Val | Met | Cys | Asp | Arg | Ala | Ile | Gly | Lys | |
| Peak | 9 | (SEQ ID NO: 8) | Lys Tyr | Leu | Ser | Gly | Val | Val | Leu | Asn | Glu | Gln | Pro | Glu |
| peak | 10 | (SEQ ID NO: 9) | Lys Leu | Asn Cys | Val Ser | Val Ile | Gly Tyr | Ser Lys | Gln | Glu | Ser | Leu | Glu | Glu |

(4) Cloning of DNA encoding AATase from sake yeast
(i) Preparation of sake yeast library Yeast cells of KYOKAI No. 7 were grown in 1 liter of a YPD medium up to O.D. 600=10, collected and washed with sterilized water. The cells were suspended in SCE solution (1M sorbitol, 0.125M EDTA, 0.1M trisodium citrate (pH 7), 0.75% 2-mercaptoethanol, 0.01% "ZYMOLYACE 100T" (SEIKAGAKU KOGYO K.K.) in a ratio of 2 ml of SCE solution per 1 g of the cells, incubated at 37° C. for about 2 hours and protoplastized completely. The resulting protoplast was suspended in Lysis Buffer (0.5M Tris hydrochloride buffer (pH 9), 0.2M EDTA, 3% sodium dodecyl sulfate (SDS)) in an ratio of 3.5 ml of the buffer per 1 g of the cells. The mixture was then stirred gently at 65° C. for 15 minutes to lyse the cells completely. After the lysis, the mixture was cooled to room temperature, a 10 ml of the mixture was cautiously placed on each of 23.5 ml of 10%–40% sucrose density gradient solution (0.8M sodium chloride, 0.02M Tris hydrochloride buffer (pH 8), 0.0M EDTA, 10%–40% sucrose) which had been previously prepared in HITACHI ultracentrifugation tubes 40PA. It was centrifuged with a HITACHI ULTRACENTRIFUGE SCP85H at 4° C. and 26,000 rpm for 3 hours. After the centrifugation, the resulted solution was recovered with a graduated pippete (komagome) in an amount of about 5 ml from the bottom of the tube. The DNA sample thus recovered was dialyzed overnight against 1 liter of a TE solution.

The chromosomal DNA thus obtained was partially digested with Sau3AI according to the method by Frischauf et al. (Methods in Enzymology, 152, 183, Academic Press, 1987), placed again on 10%–40% sucrose density gradient solution and centrifuged at 20° C. and 25,000 rpm for 22 hours. After centrifugation, the ultracentrifugation tube was pierced at the bottom with a needle, and 0.5 ml of the density and cells were grown up to O.D. 600=0.5. After the culture fluid was cooled on an ice bath, the cells were collected by centrifugation and suspended in 15 ml of an ice-cooled 10 mM magnesium sulfate solution. To 1 ml of the cells were added 0.95 ml of an SM solution (0.1M sodium chloride, 10 mM magnesium sulfate, 50 mM Tris hydrochloride buffer (pH 7.5 mM), 0.01% gelatin) and 50 μl of the packaging solution. The mixture was slightly stirred and kept at a temperature of 37° C. for 15 minutes. A 200 μl portion of the mixture was added into 7 ml of a BBL soft agar culture medium (1% Tripticase peptone (BBL), 0.5% sodium chloride, 0.5% agarose (Sigma)) which had been maintained at a temperature of 47° C. The mixture was slightly mixed and overlaid for spreading on a BBL agar plate (1% Tripticase peptone, 0.5% sodium chloride, 1.5% Bactoagar (DIFCO)) having a diameter of 15 cm.

The overlaid plate was incubated at a temperature of 37° C. for 8 hours. A phage library which contains approximately 30,000 clones having yeast chromosmal DNA fragments, on 10 overlaid agar plates were thus obtained.

The library was transferred to a nylon membrane for cloning. A hybridization transfer membrane (NEN) having a diameter of 15 cm was contacted with the overlaid agar plate for about 2 minutes to prepare two sets of the membranes on which the phages were transferred and 20 sheets in total. The membranes were placed with the surface which had been contacted with the agar plate up on a filter paper impregnated with an alkali denaturating solution (1.5M sodium chloride, 0.5N sodium hydroxide) and left standing for about 5 minutes. The membranes were then displaced on a filter paper impregnated with a neutralizing solution (3M sodium acetate (pH 5.8)), left standing for about 5 minutes, then dried at room temperature and further dried in vacuum at 80° C. for 1 hour. The agar plate from which the library had been transferred were stored at 4° C.

(ii) Synthesis and Labelling of probes

The following synthetic probes were prepared using, a DNA synthesizer "Model 380B" (manufactured by APPLIED BIOSYSTEMS) on the basis of the partial amino acid sequence of Peak 5 and Peak 2 obtained in (3):

```
Probe 5 (SEQ ID NO: 10)   Lys Tyr Glu Glu Asp Tyr
(Peak 5)              5'-AAA TAT GAA GAA GAT TAT CA-3'
                          G   C   G   G   C   C Probe 2 (SEQ ID NO: 11)   Lys Tyr Val Asn Ile
                      5'-AAA TAT GTA AAT ATT GA-3'
                          G   C   G   C   C
                                      C       A
                                      T
```

All of the synthesis reagents such as phosphoamidite were purchased from APPLIED BIOSYSTEMS and were used according to manufacturer's instructions.

The synthetic DNA thus obtained was treated with 3 ml of an 28% aqueous ammonia at 200° C. for 4 hours and then purified with an Oligonucleotide Purification Cartriges manufactured by APPLIED BIOSYSTEMS.

The two synthetic probes were individually labelled with [γ-$^{32}$P]ATP (ca. 6000 Ci/mM). Each probe DNA (ca. 250 ng) was subjected to reaction in 200 µl of a reaction solution containing 10 units of T4 polynucleotide kinase, 500 µCi of [γ-$^{32}$P]ATP and a phosphate buffer (0.1 mM spermidine, 0.1 mM EDTA, 10 mM magnesium chloride, 5 mM DTT, 50 mM Tris hydrochloride (pH 7.6)) at 37° C. for 1 hour, and kept at a temperature of 70° C. for 10 minutes. Unincorporated [γ-$^{32}$P]ATP was removed by the purification with a DE52 manufactured by WATTMAN.

(iii) Cloning by plaque hybridization

The cloning by plaque hybridization was carried out by first, second and third screenings as follows:

In the first screening, 20 sheets of the membrane on which the yeast library prepared in (4)-(i) had been transferred were dipped into 200 ml of a hybridization solution (6×SSPE (1.08M sodium chloride, 0.06M sodium phosphate, 6 mM EDTA, pH 7.4), 5×a Denhardt's solution (0.1% polyvinylpyrrolidone, 0.1% Ficoil, 0.1% bovine serum albumin), 0.5% SDS, 10 µg/ml single strand salmon sperm DNA) and incubated for prehybridization at 60° C. for 3 hours.

The [γ-$^{32}$P]ATP labelled probe 5 prepared in (4)-(ii) was kept at 95° C. for 5 minutes and cooled with ice-water. The twenty sheets of the prehybrized membrane were dipped into a mixed solution of the denatured probe 5 and 400 ml of a hybridization solution and incubated gently at 30° C. overnight to hybridize the membrane with the labelled probe 5.

The hybridization solution was discarded. In order to remove the excessive probe 5 from the membrane, the membrane was shaken gently in 400 ml of 2×SSC (0.3M sodium chloride, 0.3M sodium citrate) at 30° C. for 20 film and exposed at −80° C. overnight. As positive clones minutes. The membrane was then contacted with a X-ray 49 plaques which had sensitized both of the two sheets were subjected to the second screening.

In the second screening, these plaques on the original agar plates were picked with an aseptic Pasteur's pipette and suspended into 1 ml of SM. After A 1/1000 dilution of the suspension was prepared, 100 µl of the P2392 microbial solution was infected with a 100 µl portion of the dilution in the same manner as in the preparation of the library, mixed with 3 ml of a BBL soft agar medium and overlaid on a BBL agar plates having a diameter of 9 cm . After plaques had appeared, 49 sets of two membrane sheets to one clone were prepared in the same manner as described in (3)-(iii). The same procedure as in the first screening was repeated with the [γ-$^{32}$P]ATP labelled probe 2 which had been prepared in (4)-(ii). Fifteen plaques as the positive clones were subjected to the third screening.

In the third screening, using the [γ-$^{32}$P]ATP labelled probe 5, the same procedure as in the second screening screening was repeated. Finally, 14 positive clones were obtained.

An overnight culture of E. coli P2392 in TB medium was concentrated four times in TB medium containing 10 mM MgSO$_4$. Then 20 µl of each positive clone which had been prepared in a concentration of 10$^9$ to 10$^{10}$ plaque/ml was infected to 5 ml of this cell suspension. This infected all suspension was kept at 37° C. for 15 minutes, then inoculated into 50 ml of TB medium containing 10 mM MgSO$_4$ and cultured for 6 hours with shaking. Then, CCl$_4$ was added to the cell culture and the culture was incubated with shaking at 37° C. for 30 minutes to lyse P2392 and centrifuged at 10,000 rpm for 10 minutes to recover the supernatant. DNase (TAKARA SHUZO) and RNase (BERINGER-MANNHEIM) were added to the supernatant up to 10 µg/ml, respectively. The mixture was then kept at 37° C. for 30 minutes. After the polyethylene glycol solution (20% Polyethylene Glycol 6000, 2.5M sodium chloride) was added in an amount of 30 ml, the mixture was left standing at 4° C. overnight. Centrifugation was conducted at 10,000 rpm for 10 minutes. After the supernatant was discarded, the precipitate was suspended in 3 ml of SM. EDTA (pH 7.5 mM) and SDS were added to the suspension up to 20 mM and 0.1%, respectively. The mixture was kept then at 55° C. for 4 minutes followed by adding the phenol solution (phenol (25): chloroform (24): isoamyl alcohol (1)). The mixture was slowly stirred for 10 minutes, centrifuged 10,000 rpm for 10 minutes to recover the DNA layer (aqueous layer). After this procedure was repeated again, 0.33 ml of 3 M sodium acetate and 7.5 mM ml of ethanol were added to the aqueous layer, and the mixture was stirred and left standing at −80° C. for 30 minutes. After the mixture was centrifuged at 10,000 rpm for 10 minutes, the precipitate was rinsed with 70% ethanol, then remove 70% ethanol, and the precipitate was dried up and dissolved in 500 µl of TE. Each of the phage DNAs thus obtained was cut with a variety of restriction enzymes and compared with each other by electrophoresis. Although the fourteen positive clones appeared consist of not only those containing the whole of the DNA sequence capable of producing AATase but those having partial deletions, all of the clones were those which cloned the identical site on the. yeast chromosome. The restriction map of 6.6 kb XbaI fragment containing the whole length of the DNA sequence among these clones are shown in FIG. 3. The DNA sequencing was carried out according to the dideoxy method with a XbaI fragment which had been subcloned in pUC119 (TAKARA SHUZO). The DNA sequence of the gene encoding AATase is shown in FIG. 1 (SEQ ID NO:14).

(5) Preparation of DNA encoding AATase from brewery lager yeast

Figure 6:
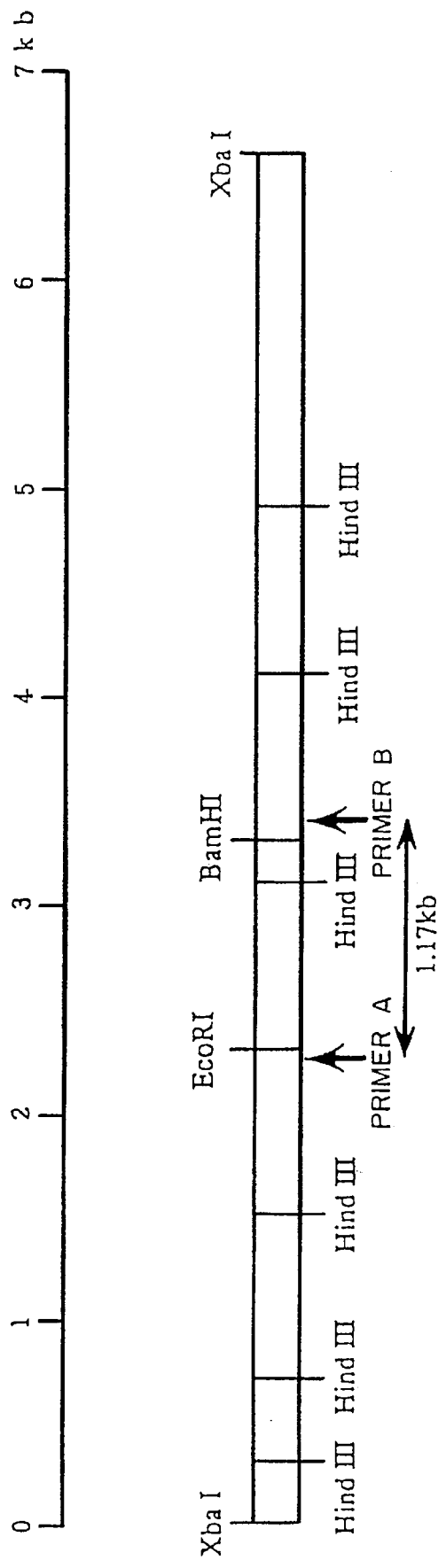
FIG. 6 shows the process for preparing the probe used for obtaining the AATase gene from the wine yeast (SEQ ID NOS 12 and 13 correspond to Primers A and B, respectively)
Figure 7:
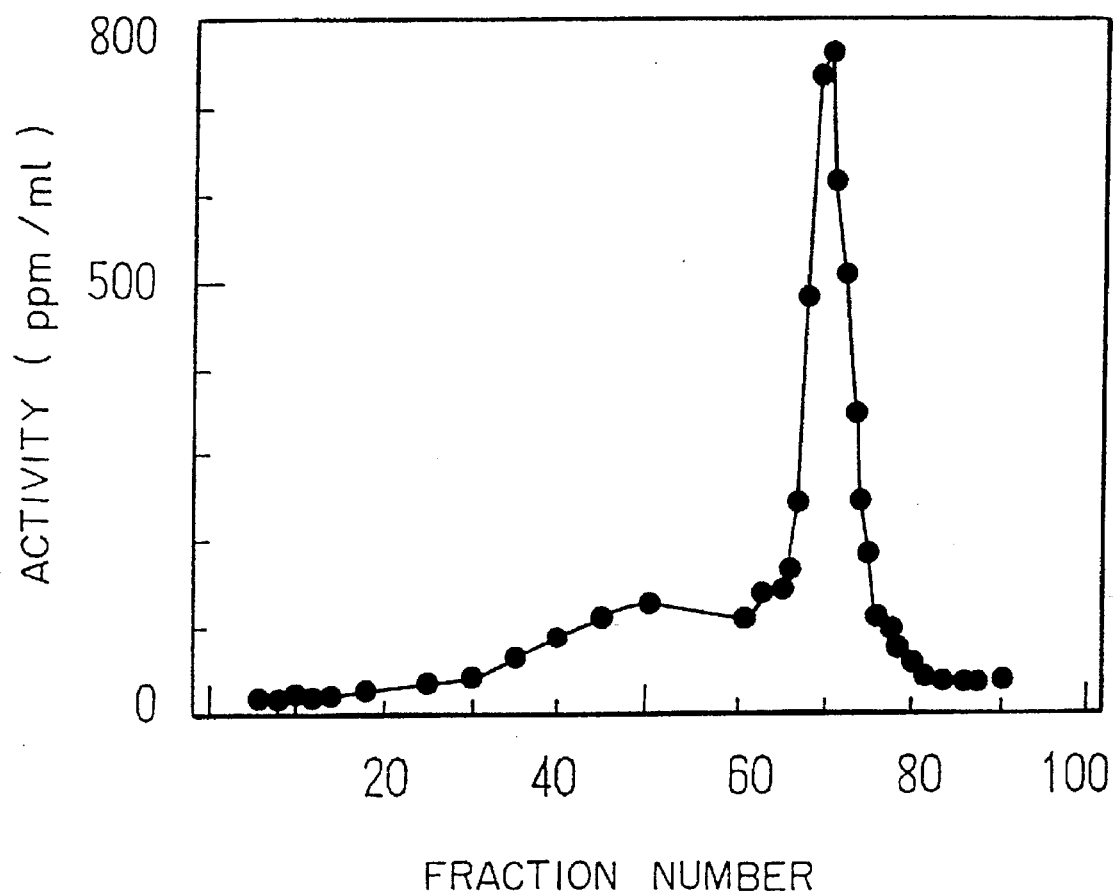
FIG. 7 shows the elution profile of an AATase active fraction by the affinity chromatography method among the purification processes according to the present invention.

Using the sake yeast AATase gene as a probe, a DNA strands hybridized with the sake yeast (KYOKAI No. 7) AATase gene were cloned from brewery lager yeast. The 1.6 kb HindIII (the range within the arrow) fragment shown in FIG. 3 (50 ng) was reacted with 100 µCi of [α-$^{32}$P]dCTP (ca. 3,000 Ci/mM) using a Multiprime Labelling Kit (AMERSHAM JAPAN K.K.). Cloning by plaque hybridization was performed with this reaction product as a probe and the brewery lager yeast library containing 30,000 phage clones prepared in the same manner as described in (4)-(i). Hybridization temperature was set at 50° C. The membranes were, gently incubated at 50° C. in 2×SSC for 30 minutes and in 0.2×SSC (0.03M sodium chloride, 3 mM sodium citrate) for 30 minutes in order to remove the excessive probes. In the first screening, 60 positive clones were obtained. These positive plaques were subjected to the second screening in the same manner as described in (4)-(iii). Hybridization was repeated with the same probe under the same condition as described above to give 30 positive clones. DNA was extracted from these positive clones and subjected to restriction analysis. The results shows that those positive clones are two groups. The restriction maps of the insert DNA of these two groups are quite different, thus it has been suggested these insert DNAs present on different locus of yeast chromosome. FIG. 6 show the restriction maps of the DNA fragment containing AATase 1 and 2. These clones are referred to hereinafter as "brewery yeast AATase 1 gene" and "brewery yeast AATase 2 gene", respectively.

The DNA sequences of the brewery yeast AATase 1 gene and the brewery yeast AATase 2 gene were determined in the same manner as described in (4)-(iii). The DNA sequences of the brewery yeast AATase 1 gene and the brewery yeast AATase 2 gene are shown in FIGS. 2 (SEQ ID NO:16) and 17 (SEQ ID NOS:12 and 13, respectively), respectively. The AATase 2 gene was a DNA fragment which produces a polypeptide having an AATase activity in either case of the DNA sequence from A to C or the DNA sequence from B to C.

Figure 11:
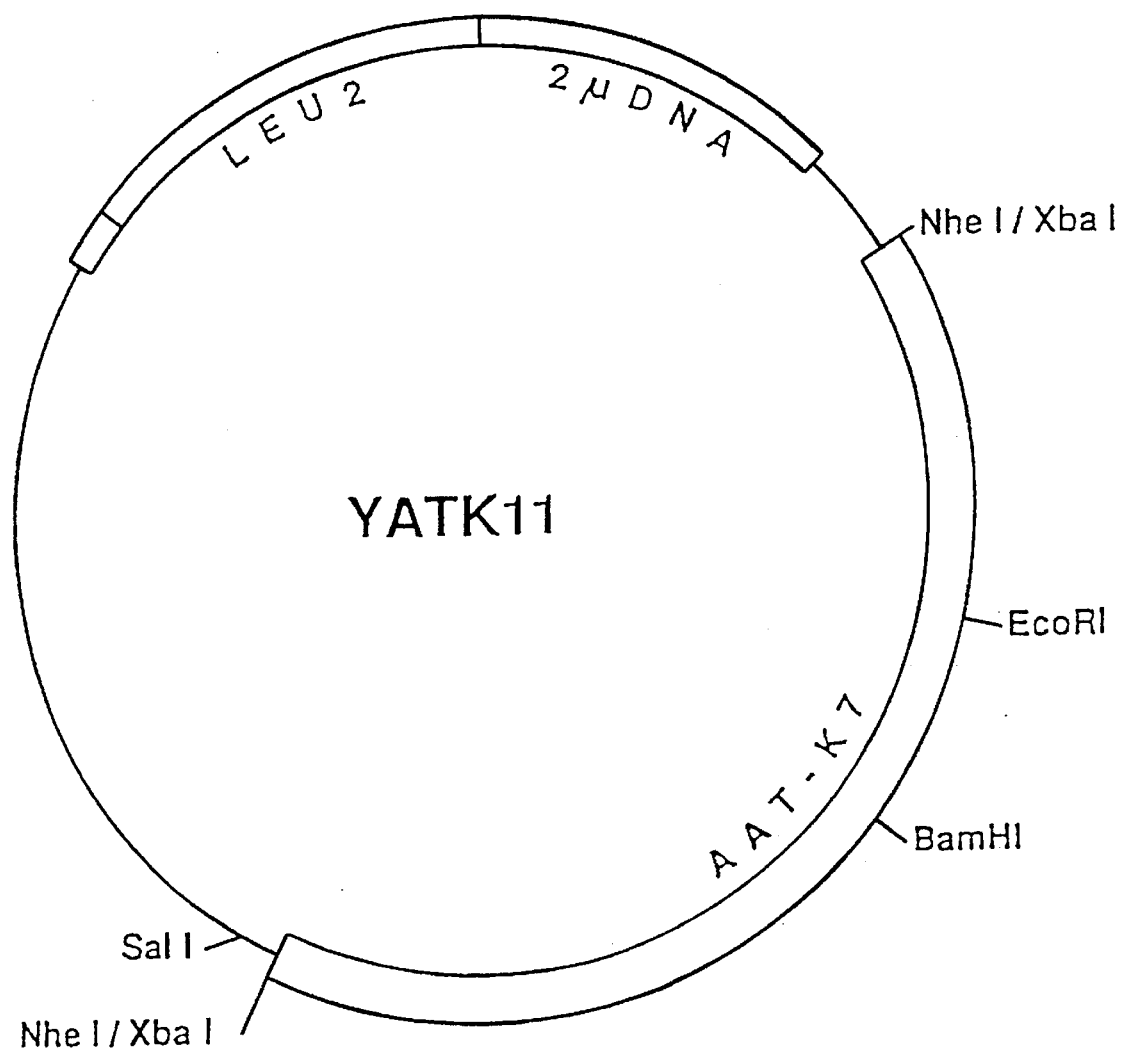
FIG. 11 shows a restriction map of the expression vector YATK11 having the AATase gene originated from a sake yeast according to the present invention.
Figure 12:
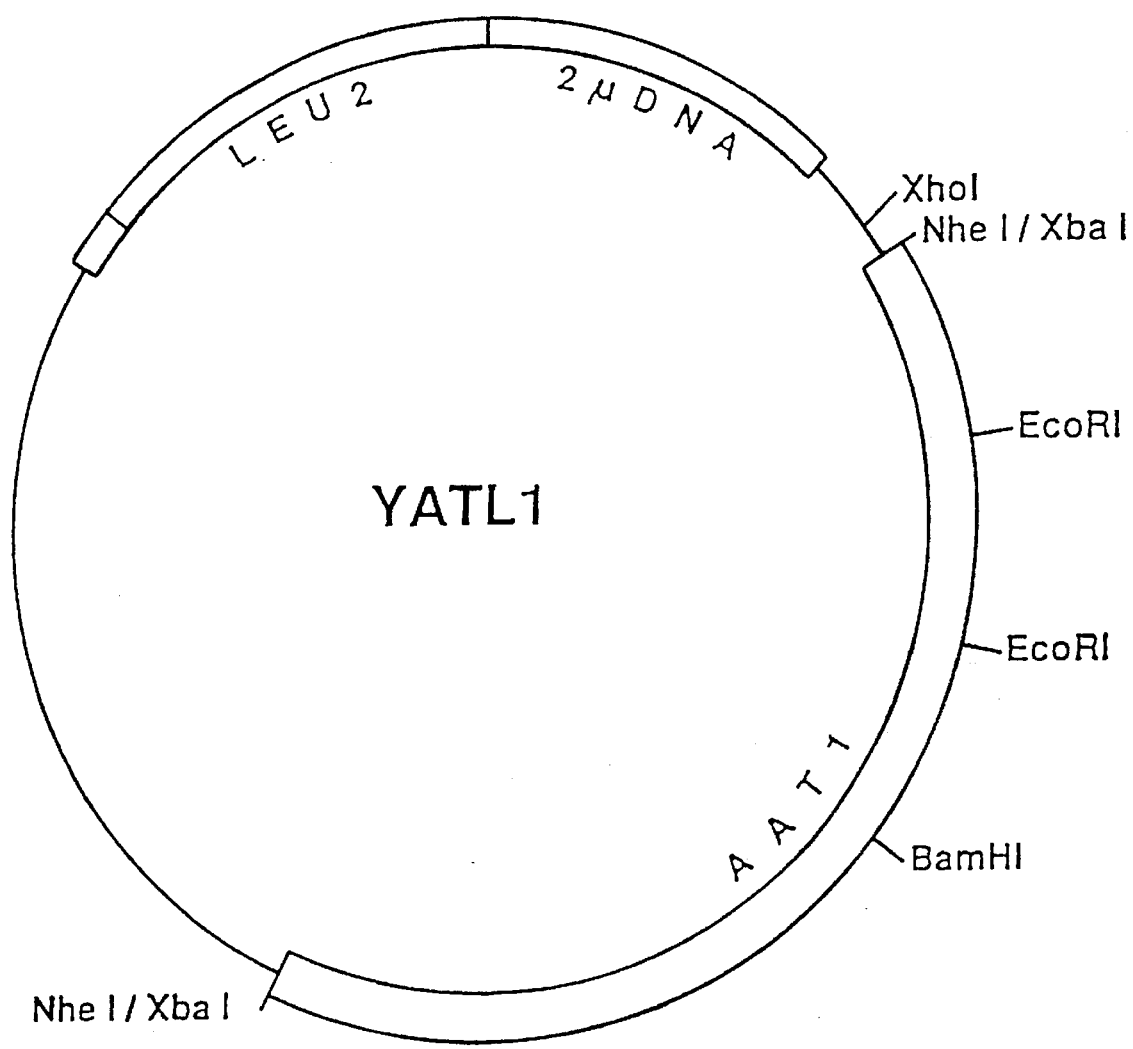
FIG. 12 shows a restriction map of the expression vector YATL1 having the AATase 1 gene originated from a brewery lager yeast according to the present invention.
Figure 13:
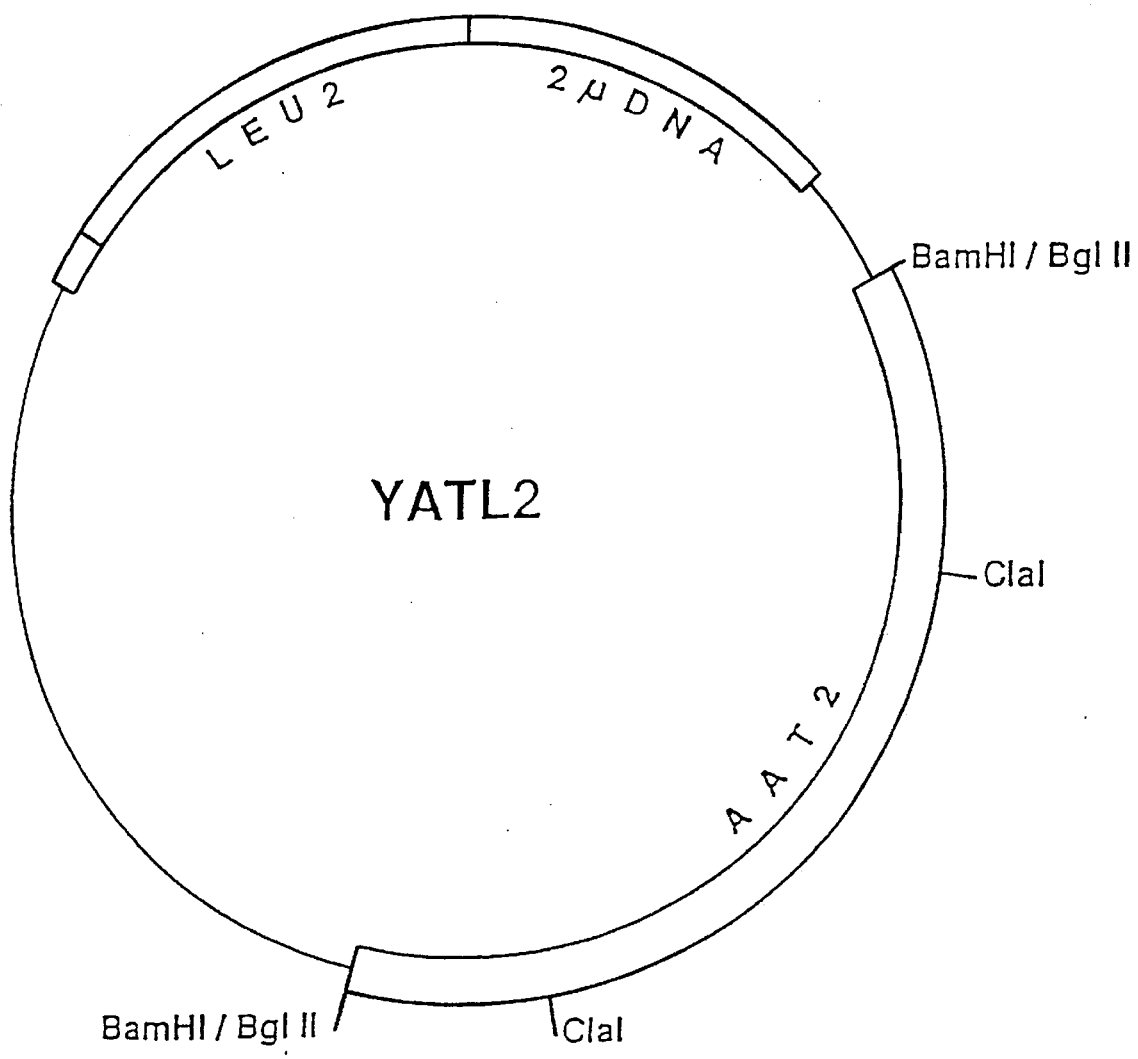
FIG. 13 shows a restriction map of the expression vector YATL2 having the AATase 2 gene originated from a brewery lager yeast according to the present invention.

(6) Preparation of a vector containing an AATase gene and cultivation of a yeast transformed by the vector (i) Construction of an expression vector for Saccharomyces cerevisiae A 6.6 kb XbaI fragment (AAT-K7) of the sake yeast AATase gene obtained in (4)-(iii) and shown in FIG. 3 was prepared. The fragment was cloned into the NheI site of the yeast vector YEp13K containing the replication origin of the yeast 2 μm DNA and the yeast LEU2 gene as a marker to construct the expression vector YATK11 (FIG. 11). In the same manner, a 6.6 kb XbaI fragment (AAT-1) of the brewery yeast AATase gene 1 obtained in (5) and shown in FIG. 4 was cloned into the NheI site of YEp13K to construct the expression vector YATL1 (FIG. 12). In addition, a 5.6 kb BglII fragment (AAT-2) of the brewery yeast AATase gene 2 shown in FIG. 4 was cloned into the BamHI site of YEp13K to construct the expression vector YATL2 (FIG. 13).

(ii) Construction of an expression vector for sake yeast KYOKAI No. 9

Figure 14:
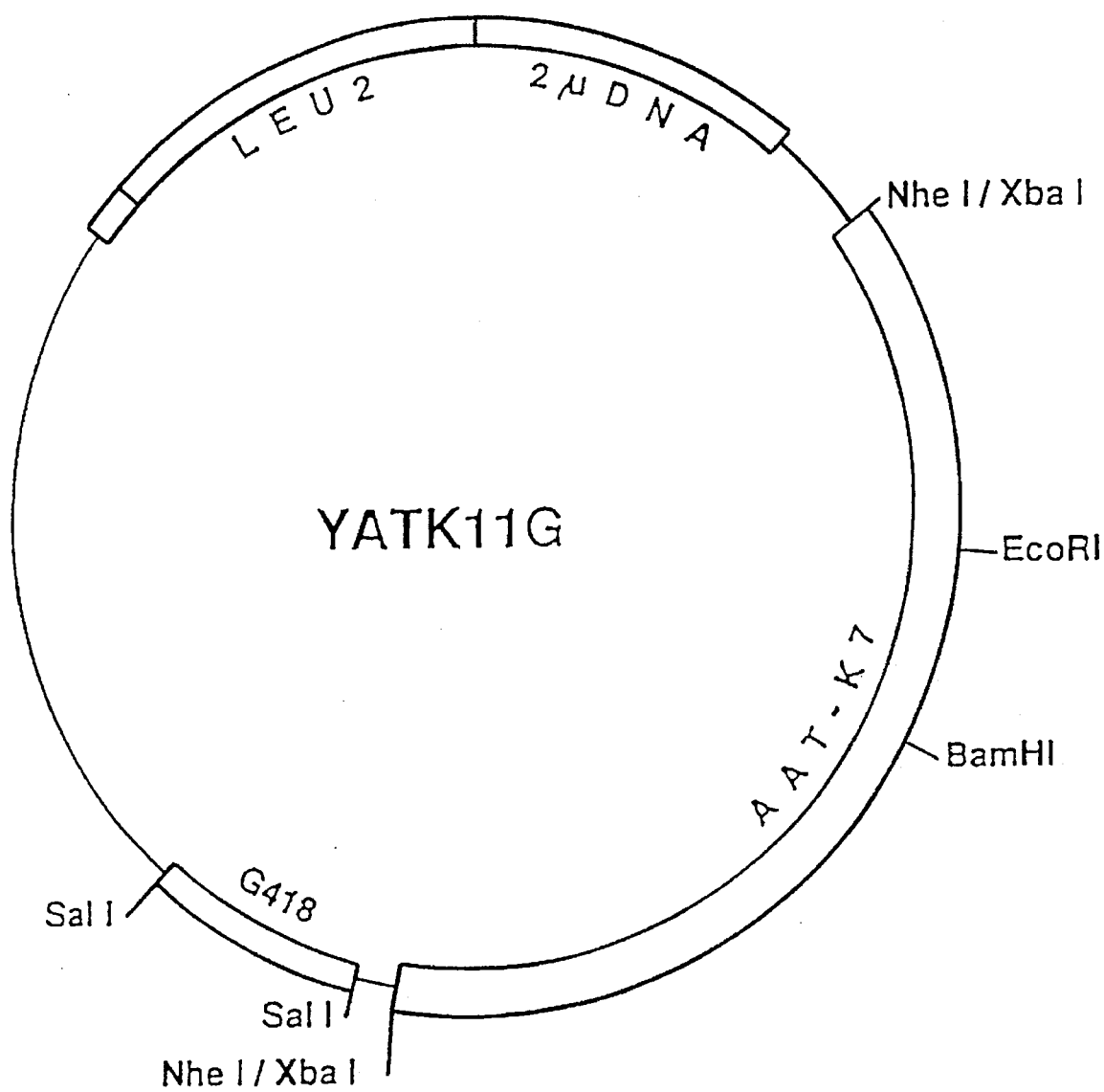
FIG. 14 shows a restriction map of the sake-yeast expression vector YATK11G having the AATase gene originated from a sake yeast according to the present invention.

Plasmid pUC4k (Pharmacia) containing a G418 resistant gene was cut with SalI. Then, the resulting fragment containing the G418 resistant gene was cloned into the SalI site of the YATK11 to construct a vector YATK11 G for transfecting the AATase gene into sake yeast (FIG. 14).

(iii) Construction of an expression vector for brewery lager yeast (iii-a) Preparation of G418 resistant marker The 2.9 kb HindIII fragment containing PGK gene (Japanese Patent Laid-Open Publication No. 26548/1990) was cloned into pUC18 (TAKARA SHUZO). Plasmid pUCPGK21 containing a PGK promoter and a terminator was shown in FIG. 16.

Figure 16:
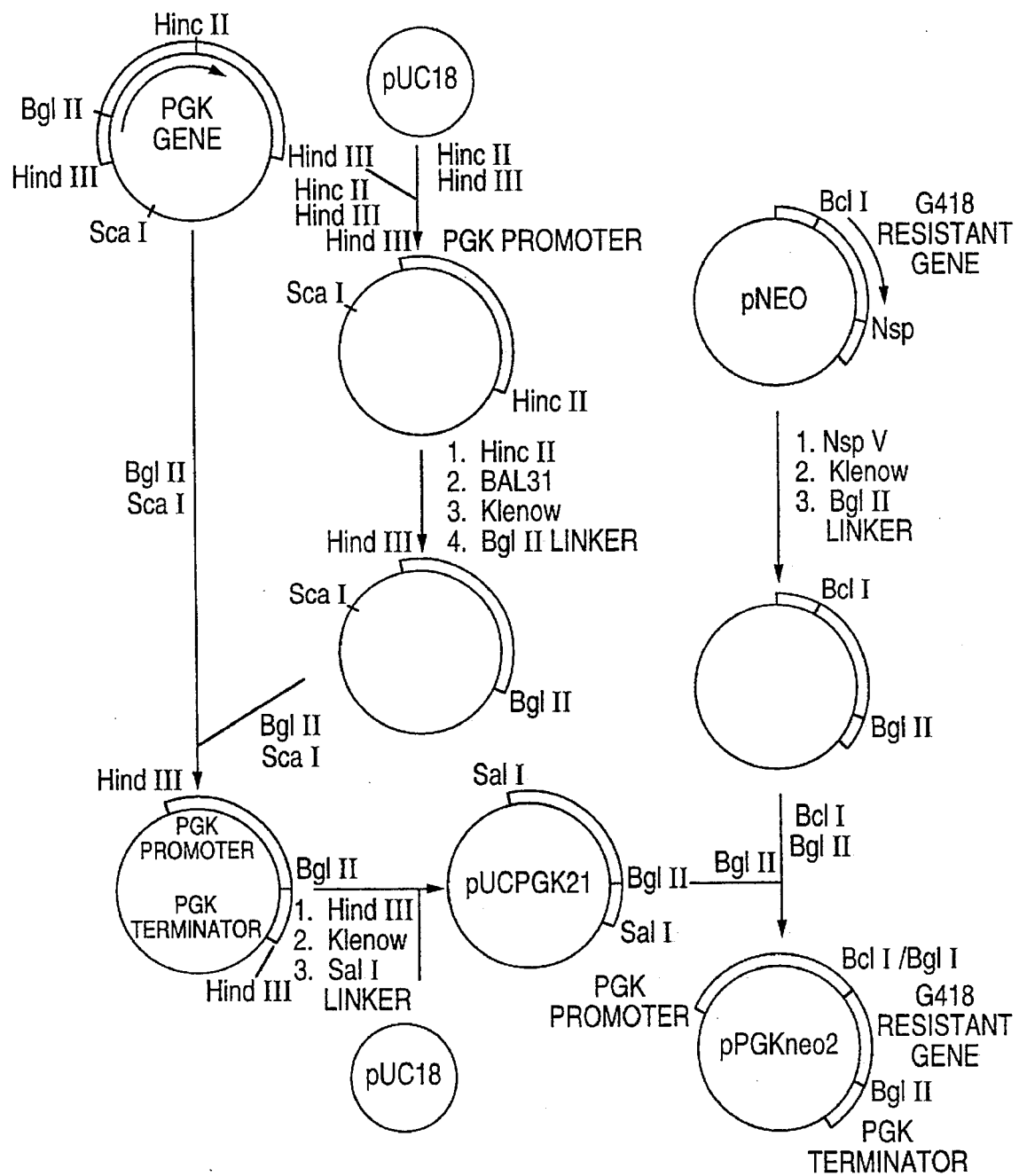
FIG. 16 shows a part of the brewery lager yeast expression vector construction.

G418 resistant gene was cloned from the plasmid pNEO (Pharmacia) into the pUCPGK21 by the process described in FIG. 16 to construct pPGKneo2.

(iii-b) Construction of expression vectors pPGKNEO2 was digested with SalI to generate the ca. 2.8 kb fragment containing the PGK promoter, the G418 resistant gene and the PGK terminator. This fragment was then cloned into the XhoI site of YATL1 to construct YATL1 G (FIG. 15).

(7) Transformation of yeasts with AATase gene

In order to confirm that the cloned AATase genes in (4)-(iii) and (5) Produces AATase, yeast cells were transformed with these vectors prepared in (6), and AATase activity of the transformants were measured. The transfection of the plasmid into Saccharomyces cereviciae TD4 (a, his, leu, ura, trp) was carried out according to the lithium acetate method (J. Bacteriol., 153, 163 (1983)) to give YATK11/TD4, YATL1/TD4 and YATL2/TD4 (SKB105 strain).

The transformant of SAKE YEAST KYOKAI NO. 9 (SKB106 strain) was obtained according to the following procedure. The strain, in to which the plasmid had been transfected by the lithium acetate method, was spread onto YPD agar plates containing G418 (300 μl/ml). The plates were incubated at 30° C. for 3 days. Colonies grown up were inoculated again in a YPD agar medium containing G418 (500 μg/ml) and cultured at 30° C. for 2 days to give the transformants.

YATL1 G was transfected into the strain 2155 of the brewery lager yeast Alfred Jorgensen Laboratory (Denmark) (AJL2155 strain) in the following procedure. The yeast was cultured with shaking in 100 ml of a YPD medium at 30° C. until O.D. 600=16. Cells were collected, rinsed once with sterilized water, then rinsed once with 135 mM Tris buffer (pH 8.0) and suspended in the same buffer so that the suspension had a microbial concentration of $2 \times 10^9$ cells/ml. To 300 μl of the suspension were added 10 μg of YATL1G, 20 μg of calf thymus DNA (Sigma) as a carrier DNA and finally 1200 μl of 35% PEG4000 (which had been subjected to sterilized filtration). The mixture was then stirred sufficiently. A 750 μl portion of the stirred fluid was poured into a cuvette for Gene Pulser (BIORAD) and subjected once to an electric pulse treatment under the conditions of 1 μF and 1000 V. The cell suspension was transferred from the cuvette to a 15 ml tube and left standing at 30° C. for 1 hour. The cells were collected by centrifugation at 3,000 rpm for 5 minutes, suspended. in 1 ml of a YPD medium and incubated at 30° C. for 4 hour. The cells were collected, suspended in 600 μl of sterilized water. A 150 μl of the suspension were spread onto YPD agar plates containing G418 (100 μg/ml). The plates were incubated at 30° C. for 3 days to obtain the transformant SKB108.

The AATase activities of the transformant into which the AATase gene had been transfected and the control strains were measured. An SD liquid medium containing a leucine-free mixed amino, acid solution (0.65% yeast nitrogen base (amino acid free; DIFCO), 2% glucose) was used for cultivating transformants of Saccharomyces cerevisiae TD4; an YPD liquid medium containing G418 (400 μg/ml) was used for cultivating transformants of sake yeast KYOKAI No. 9; a YPD medium containing G418 (10 μg/ml) was used for cultivating transformants of brewery lager yeast AJL2155 strain. A 25 ml portion of the shaking culture product at 30° C. for about 16 hours was added to 1000 ml of the culture medium and the culture was incubated at 30° C. for 12 to 18 hours under static conditions.

The preparation of a crude enzyme and the assay of its activity were performed according to the procedures described in (1)-(ii) and (1)-(i). Protein concentration was determined with a BIORAD PROTEIN ASSAY KIT (BIORAD) according to the instructions of its manual.

The results for the Saccharomyces cerevisiae TD4, the sake yeast KYOKAI No. 9 and the beer yeast AJL2155 are shown in Tables 4, 5 and 6, respectively. The results shows that the transformants of the present invention have AATase activities of 2 to 15 time higher than that of the untransformed stain. This indicates that the AATase gene according to the present invention facilely provides a strain which produces a large amount of an acetate ester such as isoamyl acetate.

TABLE 4

| Transformants | Crude enzyme activity (ppm/mg protein) |
| --- | --- |
| YEp13K/TD4 | 7.8 |
| YATK11/TD4 | 84.0 |
| YATL1/TD4 | 116.2 |
| YATL2/TD4 (SKB105) | 50.6 |

TABLE 5

| Transformants | Crude enzyme activity (ppm/mg protein) |
| --- | --- |
| K9 | 3.4 |
| YATK11G/K9 (SKB106) | 11.6 |

TABLE 6

| Transformants | Crude enzyme activity (ppm/mg protein) |
| --- | --- |
| AJL2155 | 4.1 |
| YATK11G/AJL2155 (SKB108) | 11.6 |

(8) Fermentation test of the transformants

Sake and beer were prepared by use of the yeast transformed with the AATase gene in the above (7).

(8)-(i) Production of sake with the transformant yeast

Small scale sake brewing test was carried out with 300 g rice according to the feed program as shown in Table 7. Thirty grams of malted rice (koji rice) and 110 ml of water including yeast (2×10⁷ cells/ml) (Koji rice) and lactic acid (0.35% (v/v)) were mixed and incubated at 15° C. On the second day, 35 g of steamed rice was added as the 1st feed. On the fourth day, the 2 nd feed was carried out. After fermentation for 15 days, the fermentation product was centrifuged at 8,000 rpm for 30 minutes. Esters concentration of the "sake" liquor was measured. The results are shown in Table 8. The liquor produced by the transformant of the present invention has an aromatic flavor due to an enhanced amount of acetate esters such as ethyl acetate, isoamyl acetate in comparison with the liquor produced by yeast cells of KYOKAI-K9.

TABLE 7

Feed program for small scale sake brewing

| | Seed Mash | 1st | 2nd | Total |
| --- | --- | --- | --- | --- |
| Steamed rice | | 35 g | 213 g | 248 g |
| Koji rice | 30 g | | 22 g | 52 g |
| Water | 110 ml | | 310 ml | 420 ml |

TABLE 8

| Strain | EtOH (%) | NS | Ethyl acetate |
| --- | --- | --- | --- |
| YKB106 | 18.3 | +12.1 | 38.8 |
| K-9 (Control) | 18.5 | +12.3 | 16.6 |

| Strain | ISo butanol | Isoamyl alcohol | Isoamyl acetate | Ethyl caproate |
| --- | --- | --- | --- | --- |
| YKB106 | 88.7 | 211.0 | 7.5 | 0.6 |
| K-9 (Control) | 93.3 | 230.9 | 4.4 | 0.5 |

Unit: ppm
NS: Nippon Shudo (Sake degree)

(8)-(ii) Preparation of beer with transformant yeast

After yeast was added to the wort in which the original extract content was adjusted to 11° P., the mixture was incubated at 8° C. for 8 days, centrifuged at 3,000 rpm for 10 minutes and sterilized by filtration. Esters contained in the filtrated solution was measured. The results are shown in Table 9. The transformant of the present invention produced a liquor having an enhanced amount of acetate esters such as ethyl acetate, isoamyl acetate in comparison with the liquor produced by the untransformed yeast AJL2155.

TABLE 9

| Strain | Apparent extract content (°P) | Ethyl acetate (ppm) | Isoamyl acetate (ppm) | Isoamyl alcohol (ppm) |
| --- | --- | --- | --- | --- |
| SKB108 (YATL1G) | 2.3 | 22.8 | 0.99 | 51.2 |
| AJL2155 (Control) | 2.8 | 5.9 | 0.13 | 40.0 |

(9) Preparation of DNA encoding AATase from the wine yeast

Figure 5:
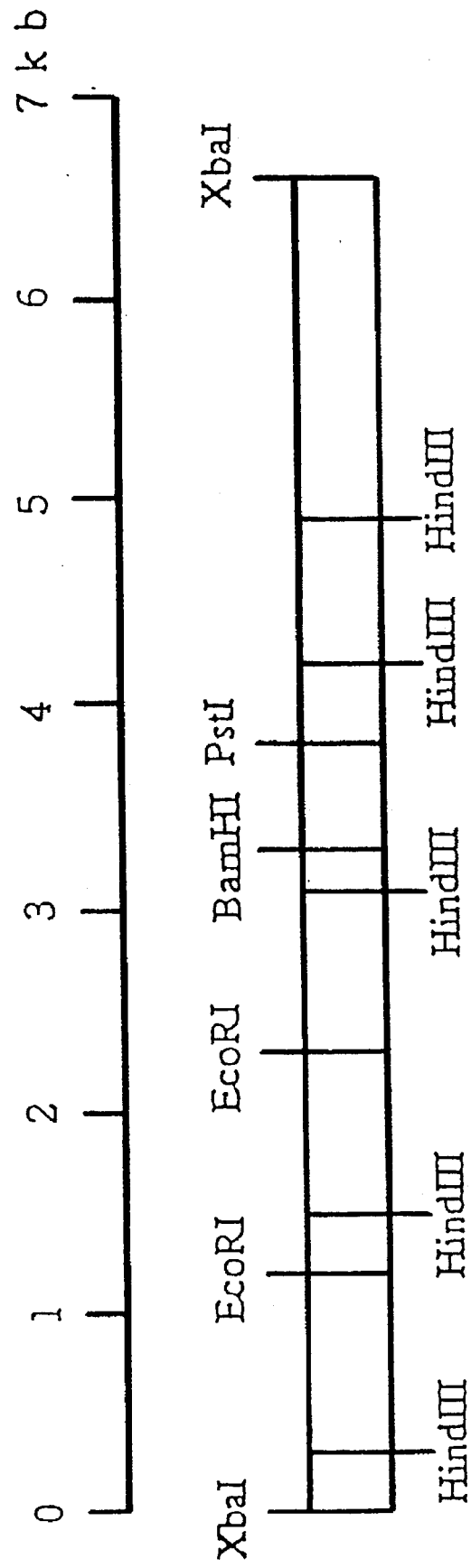
FIG. 5 shows a restriction map of the AATase originated from a wine yeast according to the present invention.

The primers A and B (SEQ ID NOS 12 and 13, respectively) which have homology to two different sites in the sake yeast AATase gene shown in FIG. 6 were synthesized. Polymerase chain reaction (PCR) was performed with Gene Amp Reagent Kit (TAKARA SHUZO) and DNA Thermal Cycler (Parkin-Elmer-Theters Instruments Co.) using chromosomal DNA of wine yeast as a template with the two primers to give a 1.17 kb DNA fragment from the position of the primer A to the position of primer B. The process consisted of 30 cycles with annealing at 50° C. for 2 minutes. The reaction mixture was applied to agarose electrophoresis. The 1.17 kb DNA fragment was purified from the gel, labelled with 100 μCi [$^{32}$P]dCTP using Nick Translation Kit (TAKARA SHUZO) and hybridized with 20,000 genome libraries of a wine yeast W-3 (YAMANASHI KOGYO GIJUTSU CENTER) prepared in the same manner as the sake yeast library. After the hybridization was carried out at 65° C., the membranes were rinsed with 2×SSC (1×SSC is 15 mM NaCl plus 1.5 mM sodium citrate) for 20 minutes, 2×SSC for 10 minutes and finally 0.1×SSC with gentle shaking at 65° C. As positive, 14 plaques were first obtained. Upon hybridizing these plaques with the 1.7 kb fragment in the same manner as the above, 7 positive plaques having a strong hybridization signal were obtained. The phage DNAs of these positive plaques were purified and subjected to restriction enzyme analysis. As a result, it was found that all of the 7 clones were of the same DNA having the restriction map shown in FIG. 5.

Deposition of the microorganisms

The microorganisms shown below related to the present invention have been deposited at Fermentation Research Institute of Agency of Industrial Science and Technology, Japan under the following deposition numbers under the Budapest Treaty on the international Recognition of the Deposit of Microorganisms for the Purpose of Patent Procedure.

| (1) SKB105 | FERM BP-3828 |
| (2) SKB106 | FERM BP-3829 |
| (3) SKB108 | FERM BP-3830 |

YATL2, YATK11 G and YATL1G can be obtained by culturing SKB105, SKB106 and SKB108, respectively, under a certain condition, extracting therefrom the total DNA of the yeast (Methods in yeast genetics, Cold Spring Harbor Laboratory, 1988), transforming *Escherichia coli* with this total DNA and finally extracting the plasmids by the alkali method (lit: Molecular clonign, Cold Spring Harbor Laboratory, 1989).

A DNA fragment containing a part of the DNA sequence from A to B (bases 233–1808 of SEQ ID No:14) of the DNA sequence shown in FIG. 1 can be obtained by digesting YATK11G with an appropriate restriction enzyme. An example of a suitable DNA sequences is 1.6 kb HindIII fragment which is indicated by a double-headed arrow in FIG. 3.

What is claimed is:

1. A process for isolating a DNA molecule encoding alcohol acetyltransferase (AATase), comprising the steps of:
   (a) preparing a DNA probe of at least 20 nucleotides which encodes a peptide fragment of the amino acid sequence of SEQ ID NO:15, and
   (b) screening a eukaryotic genomic library with said DNA probe to identify DNA molecules encoding AATase.

2. The method of claim 1, wherein said genomic library is prepared by cleaving genomic DNA using at least one enzyme or using a physical means, wherein said cleavage produces DNA fragments having about $5 \times 10^3$ nucleotides to about $30 \times 10^3$ nucleotides.

3. The method of claim 2, wherein said enzymatic cleavage is performed using Sau3AI or MboI.

4. The method of claim 2, wherein said physical means is sonication.

5. The method of claim 1, wherein said DNA probe has the nucleotide sequence of either SEQ ID NO: 10 or SEQ ID NO: 11.

6. The method of claim 1, wherein said DNA probe contains at least 20 consecutive nucleotides of SEQ ID NO:14 from nucleotide 234 to nucleotide 1808.

7. The method of claim 1, wherein said DNA probe contains at least 100 nucleotides that encode a peptide fragment of the amino acid sequence of SEQ ID NO:15.

8. The method of claim 7, wherein said DNA probe is a fragment of a DNA molecule containing the nucleotide sequence of SEQ ID NO: 14.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
    ( A ) LENGTH: 6 amino acids
    ( B ) TYPE: amino acid
    ( D ) TOPOLOGY: linear ( x i ) SEQUENCE DESCRIPTION: SEQ ID NO:1:

Lys Tyr Val Asn Ile Asp
  1               5

( 2 ) INFORMATION FOR SEQ ID NO:2:

( i ) SEQUENCE CHARACTERISTICS:
    ( A ) LENGTH: 11 amino acids
    ( B ) TYPE: amino acid
    ( D ) TOPOLOGY: linear ( x i ) SEQUENCE DESCRIPTION: SEQ ID NO:2:

Lys Asn Gln Ala Pro Val Gln Gln Glu Cys Leu
  1               5                   10

( 2 ) INFORMATION FOR SEQ ID NO:3:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:3:

Lys Gly Met Asn Ile Val Val Ala Ser
  1               5

( 2 ) INFORMATION FOR SEQ ID NO:4:

( i ) SEQUENCE CHARACTERISTICS:
    ( A ) LENGTH: 11 amino acids
    ( B ) TYPE: amino acid
    ( D ) TOPOLOGY: linear ( x i ) SEQUENCE DESCRIPTION: SEQ ID NO:4:

Lys Tyr Glu Glu Asp Tyr Gln Leu Leu Arg Lys
  1               5                   10

( 2 ) INFORMATION FOR SEQ ID NO:5:

( i ) SEQUENCE CHARACTERISTICS:

(A) LENGTH: 8 amino acids
                (B) TYPE: amino acid
                (D) TOPOLOGY: linear (xi) SEQUENCE DESCRIPTION: SEQ ID NO:5:

Lys  Gln  Ile  Leu  Glu  Glu  Phe  Lys
    1                  5

(2) INFORMATION FOR SEQ ID NO:6:

(i) SEQUENCE CHARACTERISTICS:
                (A) LENGTH: 7 amino acids
                (B) TYPE: amino acid
                (D) TOPOLOGY: linear (xi) SEQUENCE DESCRIPTION: SEQ ID NO:6:

Lys  Leu  Asp  Tyr  Ile  Phe  Lys
    1                  5

(2) INFORMATION FOR SEQ ID NO:7:

(i) SEQUENCE CHARACTERISTICS:
                (A) LENGTH: 10 amino acids
                (B) TYPE: amino acid
                (D) TOPOLOGY: linear (xi) SEQUENCE DESCRIPTION: SEQ ID NO:7:

Lys  Val  Met  Cys  Asp  Arg  Ala  Ile  Gly  Lys
    1                  5                        10

(2) INFORMATION FOR SEQ ID NO:8:

(i) SEQUENCE CHARACTERISTICS:
                (A) LENGTH: 13 amino acids
                (B) TYPE: amino acid
                (D) TOPOLOGY: linear (xi) SEQUENCE DESCRIPTION: SEQ ID NO:8:

Lys  Leu  Ser  Gly  Val  Val  Leu  Asn  Glu  Gln  Pro  Glu  Tyr
    1                  5                        10

(2) INFORMATION FOR SEQ ID NO:9:

(i) SEQUENCE CHARACTERISTICS:
                (A) LENGTH: 18 amino acids
                (B) TYPE: amino acid
                (D) TOPOLOGY: linear (xi) SEQUENCE DESCRIPTION: SEQ ID NO:9:

Lys  Asn  Val  Val  Gly  Ser  Gln  Glu  Ser  Leu  Glu  Glu  Leu  Cys  Ser  Ile
    1                  5                        10                       15

Tyr  Lys (2) INFORMATION FOR SEQ ID NO:10:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (xi) SEQUENCE DESCRIPTION: SEQ ID NO:10:

AARTAY GARG ARGA Y-
TAYCA                                                                                           20

(2) INFORMATION FOR SEQ ID NO:11:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

```
AARTAYGTNA AYATHGA                                                     17
```

( 2 ) INFORMATION FOR SEQ ID NO:12:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

```
CTCAATGAAC AACCTGAG                                                    18
```

( 2 ) INFORMATION FOR SEQ ID NO:13:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

```
TCTTCGAGAG ATTCTTGG                                                    18
```

( 2 ) INFORMATION FOR SEQ ID NO:14:

( i ) SEQUENCE CHARACTERISTICS:
    ( A ) LENGTH: 1923 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 234..1811

( x i ) SEQUENCE DESCRIPTION: SEQ ID NO:14:

```
AGCGTGTGAG GACTACTCAT TGGCTTGCGA TTTACGGTTT TTATATTTTT TGCCGCACAT       60

CATTTTTGG CCTGGTATTG TCATCGCGTT GAGCGGACTC TGAATATAAT CCTATTGTTT       120

TTTATGGATC TCTGGAAGCG TCTTTTTGAA GCCAACCCAA CAAAAATTCG AGACAAGAAA      180

ATAAAAAACG GCACTTCATC AGTATCACAA ATACCATCAA TTTATCAGCT CTC ATG         236
                                                          Met
                                                           1

AAT GAA ATC GAT GAG AAA AAT CAG GCC CCC GTG CAA CAA GAA TGC CTG        284
Asn Glu Ile Asp Glu Lys Asn Gln Ala Pro Val Gln Gln Glu Cys Leu
         5                  10                  15

AAA GAG ATG ATT CAG AAT GGG CAT GCT CGG CGT ATG GGA TCT GTT GAA        332
Lys Glu Met Ile Gln Asn Gly His Ala Arg Arg Met Gly Ser Val Glu
             20                  25                  30

GAT CTG TAT GTT GCT CTC AAC AGA CAA AAC TTA TAT CGG AAC TTC TGC        380
Asp Leu Tyr Val Ala Leu Asn Arg Gln Asn Leu Tyr Arg Asn Phe Cys
         35                  40                  45

ACA TAT GGA GAA TTG AGT GAT TAC TGT ACT AGG GAT CAG CTC ACA TTA        428
Thr Tyr Gly Glu Leu Ser Asp Tyr Cys Thr Arg Asp Gln Leu Thr Leu
 50                  55                  60                  65

GCT TTG AGG GAA ATC TGC CTG AAA AAT CCA ACT CTT TTA CAT ATT GTT        476
Ala Leu Arg Glu Ile Cys Leu Lys Asn Pro Thr Leu Leu His Ile Val
             70                  75                   80
```

| | | | | | | | | | | | | | | | | |
|---|---|---|---|---|---|---|---|---|---|---|---|---|---|---|---|---|
| CTA | CCA | ATA | AGA | TGG | CCA | AAT | CAT | GAA | AAT | TAT | TAT | CGC | AGT | TCC | GAA | 524 |
| Leu | Pro | Ile | Arg | Trp | Pro | Asn | His | Glu | Asn | Tyr | Tyr | Arg | Ser | Ser | Glu | |
| | | 85 | | | | | 90 | | | | | 95 | | | | |
| TAC | TAT | TCA | CGG | CCA | CAT | CCA | GTG | CAT | GAT | TAT | ATT | TCA | GTA | TTA | CAG | 572 |
| Tyr | Tyr | Ser | Arg | Pro | His | Pro | Val | His | Asp | Tyr | Ile | Ser | Val | Leu | Gln | |
| | | 100 | | | | 105 | | | | | 110 | | | | | |
| GAA | TTG | AAA | CTG | AGT | GGT | GTG | GTT | CTC | AAT | GAA | CAA | CCT | GAG | TAC | AGT | 620 |
| Glu | Leu | Lys | Leu | Ser | Gly | Val | Val | Leu | Asn | Glu | Gln | Pro | Glu | Tyr | Ser | |
| 115 | | | | | 120 | | | | | 125 | | | | | | |
| GCA | GTA | ATG | AAG | CAA | ATA | TTA | GAA | GAA | TTC | AAA | AAT | AGT | AAG | GGT | TCC | 668 |
| Ala | Val | Met | Lys | Gln | Ile | Leu | Glu | Glu | Phe | Lys | Asn | Ser | Lys | Gly | Ser | |
| 130 | | | | | 135 | | | | 140 | | | | | 145 | | |
| TAT | ACT | GCA | AAA | ATT | TTT | AAA | CTT | ACT | ACC | ACT | TTG | ACT | ATT | CCT | TAC | 716 |
| Tyr | Thr | Ala | Lys | Ile | Phe | Lys | Leu | Thr | Thr | Thr | Leu | Thr | Ile | Pro | Tyr | |
| | | | | 150 | | | | | 155 | | | | | 160 | | |
| TTT | GGA | CCA | ACA | GGA | CCG | AGT | TGG | CGG | CTA | ATT | TGT | CTT | CCA | GAA | GAG | 764 |
| Phe | Gly | Pro | Thr | Gly | Pro | Ser | Trp | Arg | Leu | Ile | Cys | Leu | Pro | Glu | Glu | |
| | | | 165 | | | | | 170 | | | | | 175 | | | |
| CAC | ACA | GAA | AAG | TGG | AAA | AAA | TTT | ATC | TTT | GTA | TCT | AAT | CAT | TGC | ATG | 812 |
| His | Thr | Glu | Lys | Trp | Lys | Lys | Phe | Ile | Phe | Val | Ser | Asn | His | Cys | Met | |
| | | 180 | | | | | 185 | | | | | 190 | | | | |
| TCT | GAT | GGT | CGG | TCT | TCG | ATC | CAC | TTT | TTT | CAT | GAT | TTA | AGA | GAC | GAA | 860 |
| Ser | Asp | Gly | Arg | Ser | Ser | Ile | His | Phe | Phe | His | Asp | Leu | Arg | Asp | Glu | |
| | 195 | | | | | 200 | | | | | 205 | | | | | |
| TTA | AAT | AAT | ATT | AAA | ACT | CCA | CCA | AAA | AAA | TTA | GAT | TAC | ATT | TTC | AAG | 908 |
| Leu | Asn | Asn | Ile | Lys | Thr | Pro | Pro | Lys | Lys | Leu | Asp | Tyr | Ile | Phe | Lys | |
| 210 | | | | | 215 | | | | | 220 | | | | | 225 | |
| TAC | GAG | GAG | GAT | TAC | CAA | TTG | TTG | AGG | AAA | CTT | CCA | GAA | CCG | ATC | GAA | 956 |
| Tyr | Glu | Glu | Asp | Tyr | Gln | Leu | Leu | Arg | Lys | Leu | Pro | Glu | Pro | Ile | Glu | |
| | | | | 230 | | | | | 235 | | | | | 240 | | |
| AAG | GTG | ATA | GAC | TTT | AGA | CCA | CCG | TAC | TTG | TTT | ATT | CCG | AAG | TCA | CTT | 1004 |
| Lys | Val | Ile | Asp | Phe | Arg | Pro | Pro | Tyr | Leu | Phe | Ile | Pro | Lys | Ser | Leu | |
| | | | 245 | | | | | 250 | | | | | 255 | | | |
| CTT | TCG | GGT | TTC | ATC | TAC | AAT | CAT | TTG | AGA | TTT | TCT | TCA | AAA | GGT | GTC | 1052 |
| Leu | Ser | Gly | Phe | Ile | Tyr | Asn | His | Leu | Arg | Phe | Ser | Ser | Lys | Gly | Val | |
| | | 260 | | | | | 265 | | | | | 270 | | | | |
| TGT | ATG | AGA | ATG | GAT | GAT | GTG | GAA | AAA | ACC | GAT | GAT | GTT | GTC | ACC | GAG | 1100 |
| Cys | Met | Arg | Met | Asp | Asp | Val | Glu | Lys | Thr | Asp | Asp | Val | Val | Thr | Glu | |
| 275 | | | | | 280 | | | | | 285 | | | | | | |
| ATC | ATC | AAT | ATT | TCA | CCA | ACA | GAA | TTT | CAA | GCG | ATT | AAA | GCA | AAT | ATT | 1148 |
| Ile | Ile | Asn | Ile | Ser | Pro | Thr | Glu | Phe | Gln | Ala | Ile | Lys | Ala | Asn | Ile | |
| 290 | | | | | 295 | | | | | 300 | | | | | 305 | |
| AAA | TCA | AAT | ATC | CAA | GGT | AAG | TGT | ACT | ATC | ACT | CCG | TTT | TTA | CAT | GTT | 1196 |
| Lys | Ser | Asn | Ile | Gln | Gly | Lys | Cys | Thr | Ile | Thr | Pro | Phe | Leu | His | Val | |
| | | | | 310 | | | | | 315 | | | | | 320 | | |
| TGT | TGG | TTT | GTA | TCT | CTT | CAT | AAA | TGG | GGT | AAA | TTT | TTC | AAA | CCA | TTG | 1244 |
| Cys | Trp | Phe | Val | Ser | Leu | His | Lys | Trp | Gly | Lys | Phe | Phe | Lys | Pro | Leu | |
| | | | 325 | | | | | 330 | | | | | 335 | | | |
| AAC | TTC | GAA | TGG | CTT | ACG | GAT | ATT | TTT | ATC | CCC | GCA | GAT | TGC | CGC | TCA | 1292 |
| Asn | Phe | Glu | Trp | Leu | Thr | Asp | Ile | Phe | Ile | Pro | Ala | Asp | Cys | Arg | Ser | |
| | | 340 | | | | | 345 | | | | | 350 | | | | |
| CAA | CTA | CCA | GAT | GAT | GAT | GAA | ATG | AGA | CAG | ATG | TAC | AGA | TAT | GGC | GCT | 1340 |
| Gln | Leu | Pro | Asp | Asp | Asp | Glu | Met | Arg | Gln | Met | Tyr | Arg | Tyr | Gly | Ala | |
| 355 | | | | | 360 | | | | | 365 | | | | | | |
| AAC | GTT | GGA | TTT | ATT | GAC | TTC | ACC | CCA | TGG | ATA | AGC | GAA | TTT | GAC | ATG | 1388 |
| Asn | Val | Gly | Phe | Ile | Asp | Phe | Thr | Pro | Trp | Ile | Ser | Glu | Phe | Asp | Met | |
| 370 | | | | 375 | | | | | 380 | | | | | 385 | | |
| AAT | GAT | AAC | AAA | GAA | AAA | TTT | TGG | CCA | CTT | ATT | GAG | CAC | TAC | CAT | GAA | 1436 |
| Asn | Asp | Asn | Lys | Glu | Lys | Phe | Trp | Pro | Leu | Ile | Glu | His | Tyr | His | Glu | |
| | | | | 390 | | | | | 395 | | | | | 400 | | |

```
GTA ATT TCG GAA GCT TTA AGA AAT AAA AAG CAC CTC CAT GGC TTA GGG     1484
Val Ile Ser Glu Ala Leu Arg Asn Lys Lys His Leu His Gly Leu Gly
            405                 410                 415

TTC AAT ATA CAA GGC TTC GTT CAA AAA TAT GTG AAT ATT GAC AAG GTA     1532
Phe Asn Ile Gln Gly Phe Val Gln Lys Tyr Val Asn Ile Asp Lys Val
            420                 425                 430

ATG TGC GAT CGT GCC ATC GGG AAA AGA CGC GGA GGT ACA TTG TTA AGC     1580
Met Cys Asp Arg Ala Ile Gly Lys Arg Arg Gly Gly Thr Leu Leu Ser
            435                 440                 445

AAT GTA GGT CTG TTT AAT CAG TTA GAG GAG CCC GAT GCC AAA TAT TCT     1628
Asn Val Gly Leu Phe Asn Gln Leu Glu Glu Pro Asp Ala Lys Tyr Ser
450                 455                 460                 465

ATA TGC GAT TTG GCA TTT GGC CAA TTT CAA GGA TCC TGG CAC CAA GCA     1676
Ile Cys Asp Leu Ala Phe Gly Gln Phe Gln Gly Ser Trp His Gln Ala
            470                 475                 480

TTT TCC TTG GGT GTT TGT TCG ACT AAT GTA AAG GGG ATG AAT ATT GTT     1724
Phe Ser Leu Gly Val Cys Ser Thr Asn Val Lys Gly Met Asn Ile Val
            485                 490                 495

GTT GCT TCA ACA AAA AAT GTT GTT GGT AGC CAA GAA TCT CTC GAA GAG     1772
Val Ala Ser Thr Lys Asn Val Val Gly Ser Gln Glu Ser Leu Glu Glu
            500                 505                 510

CTT TGC TCC ATT TAT AAA GCT CTC CTT TTA GGC CCT TAGATCTCAC          1818
Leu Cys Ser Ile Tyr Lys Ala Leu Leu Leu Gly Pro
            515                 520                 525

ATGATGCTTG ACTGATATTA TTCGACAATA TGATTATGTC GTGTAAATAA CCCACTTTCA   1878

TGTTGTCACT CCCTCGGCTT TGGTTGGTTA AAGGGACTTA TTGGT                   1923

( 2 ) INFORMATION FOR SEQ ID NO:15:

( i ) SEQUENCE CHARACTERISTICS:
          ( A ) LENGTH: 525 amino acids
          ( B ) TYPE: amino acid
          ( D ) TOPOLOGY: linear ( i i ) MOLECULE TYPE: protein ( x i ) SEQUENCE DESCRIPTION: SEQ ID NO:15:

Met Asn Glu Ile Asp Glu Lys Asn Gln Ala Pro Val Gln Gln Glu Cys
 1               5                  10                  15

Leu Lys Glu Met Ile Gln Asn Gly His Ala Arg Arg Met Gly Ser Val
                20                  25                  30

Glu Asp Leu Tyr Val Ala Leu Asn Arg Gln Asn Leu Tyr Arg Asn Phe
             35                  40                  45

Cys Thr Tyr Gly Glu Leu Ser Asp Tyr Cys Thr Arg Asp Gln Leu Thr
         50                  55                  60

Leu Ala Leu Arg Glu Ile Cys Leu Lys Asn Pro Thr Leu Leu His Ile
 65                  70                  75                  80

Val Leu Pro Ile Arg Trp Pro Asn His Glu Asn Tyr Tyr Arg Ser Ser
                 85                  90                  95

Glu Tyr Tyr Ser Arg Pro His Pro Val His Asp Tyr Ile Ser Val Leu
                100                 105                 110

Gln Glu Leu Lys Leu Ser Gly Val Val Leu Asn Glu Gln Pro Glu Tyr
            115                 120                 125

Ser Ala Val Met Lys Gln Ile Leu Glu Glu Phe Lys Asn Ser Lys Gly
            130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
```

|     |     |     |     | 165 |     |     |     |     |     | 170 |     |     |     |     | 175 |     |
|-----|-----|-----|-----|-----|-----|-----|-----|-----|-----|-----|-----|-----|-----|-----|-----|-----|

Glu His Thr Glu Lys Trp Lys Lys Phe Ile Phe Val Ser Asn His Cys
            180                 185                 190

Met Ser Asp Gly Arg Ser Ser Ile His Phe Phe His Asp Leu Arg Asp
        195             200             205

Glu Leu Asn Asn Ile Lys Thr Pro Pro Lys Lys Leu Asp Tyr Ile Phe
        210             215             220

Lys Tyr Glu Glu Asp Tyr Gln Leu Leu Arg Lys Leu Pro Glu Pro Ile
225                 230             235             240

Glu Lys Val Ile Asp Phe Arg Pro Pro Tyr Leu Phe Ile Pro Lys Ser
                245             250             255

Leu Leu Ser Gly Phe Ile Tyr Asn His Leu Arg Phe Ser Ser Lys Gly
            260             265             270

Val Cys Met Arg Met Asp Asp Val Glu Lys Thr Asp Asp Val Val Thr
            275             280             285

Glu Ile Ile Asn Ile Ser Pro Thr Glu Phe Gln Ala Ile Lys Ala Asn
    290             295             300

Ile Lys Ser Asn Ile Gln Gly Lys Cys Thr Ile Thr Pro Phe Leu His
305             310             315             320

Val Cys Trp Phe Val Ser Leu His Lys Trp Gly Lys Phe Phe Lys Pro
                325             330             335

Leu Asn Phe Glu Trp Leu Thr Asp Ile Phe Ile Pro Ala Asp Cys Arg
            340             345             350

Ser Gln Leu Pro Asp Asp Asp Glu Met Arg Gln Met Tyr Arg Tyr Gly
        355             360             365

Ala Asn Val Gly Phe Ile Asp Phe Thr Pro Trp Ile Ser Glu Phe Asp
    370             375             380

Met Asn Asp Asn Lys Glu Lys Phe Trp Pro Leu Ile Glu His Tyr His
385             390             395             400

Glu Val Ile Ser Glu Ala Leu Arg Asn Lys Lys His Leu His Gly Leu
            405             410             415

Gly Phe Asn Ile Gln Gly Phe Val Gln Lys Tyr Val Asn Ile Asp Lys
            420             425             430

Val Met Cys Asp Arg Ala Ile Gly Lys Arg Arg Gly Gly Thr Leu Leu
        435             440             445

Ser Asn Val Gly Leu Phe Asn Gln Leu Glu Glu Pro Asp Ala Lys Tyr
    450             455             460

Ser Ile Cys Asp Leu Ala Phe Gly Gln Phe Gln Gly Ser Trp His Gln
465             470             475             480

Ala Phe Ser Leu Gly Val Cys Ser Thr Asn Val Lys Gly Met Asn Ile
            485             490             495

Val Val Ala Ser Thr Lys Asn Val Val Gly Ser Gln Glu Ser Leu Glu
            500             505             510

Glu Leu Cys Ser Ile Tyr Lys Ala Leu Leu Leu Gly Pro
        515             520             525

( 2 ) INFORMATION FOR SEQ ID NO:16:

( i ) SEQUENCE CHARACTERISTICS:
        ( A ) LENGTH: 1974 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 346..1923

( x i ) SEQUENCE DESCRIPTION: SEQ ID NO:16:

```
GTAGCTTCAT TGTTGGCAC AGGACTATTC CACCCTTAGA ATTGACTTTT TGGACATTGA          60

GCTAAGGTTC AATGCACTCG ATGGTCTTCT CACTTCCGAA TATATAGATC TAGCGTGTGA         120

GGACTACTCA TTGGCTTGCG ATTTACGGTT TTTATATTTT TTGCCGCACA TCATTTTTTG         180

GCCTGGTATT GTCATCGCGG TTGAGCGGAC TCTGAATATA ATCCTATTGT TTTTTATGGA         240

TCTCTGGAAG CGTCTTTTTG AAGCCAACCC AACAAAAATT CGAGACAAGA AAATAAAAAA         300

CGGCACTTCA TCAGTATCAC AAATACCATC AATTTATCAG CTCTC ATG AAT GAA            354
                                                  Met Asn Glu
                                                   1
```

| ATC GAT GAG AAA AAT CAG GCC CCC GTG CAA CAA GAA TGC CTG AAA GAG | 402 |
| Ile Asp Glu Lys Asn Gln Ala Pro Val Gln Gln Glu Cys Leu Lys Glu |     |
|     5           10              15                              |     |

| ATG ATT CAG AAT GGG CAT GCT CGG CGT ATG GGA TCT GTT GAA GAT CTG | 450 |
| Met Ile Gln Asn Gly His Ala Arg Arg Met Gly Ser Val Glu Asp Leu |     |
| 20           25              30              35                 |     |

| TAT GTT GCT CTC AAC AGA CAA AAC TTA TAT CGA AAC TTC TGC ACA TAT | 498 |
| Tyr Val Ala Leu Asn Arg Gln Asn Leu Tyr Arg Asn Phe Cys Thr Tyr |     |
|             40              45              50                  |     |

| GGA GAA TTG AGT GAT TAC TGT ACT AGG GAT CAG CTC ACA TTA GCT TTG | 546 |
| Gly Glu Leu Ser Asp Tyr Cys Thr Arg Asp Gln Leu Thr Leu Ala Leu |     |
|         55              60              65                      |     |

| AGG GAA ATC TGC CTG AAA AAT CCA ACT CTT TTA CAT ATT GTT CTA CCA | 594 |
| Arg Glu Ile Cys Leu Lys Asn Pro Thr Leu Leu His Ile Val Leu Pro |     |
|     70              75              80                          |     |

| ACA AGA TGG CCA AAT CAT GAA AAT TAT TAT CGC AGT TCC GAA TAC TAT | 642 |
| Thr Arg Trp Pro Asn His Glu Asn Tyr Tyr Arg Ser Ser Glu Tyr Tyr |     |
| 85              90              95                              |     |

| TCA CGG CCA CAT CCA GTG CAT GAT TAT ATC TCA GTA TTA CAA GAA TTG | 690 |
| Ser Arg Pro His Pro Val His Asp Tyr Ile Ser Val Leu Gln Glu Leu |     |
| 100             105             110             115             |     |

| AAA CTG AGT GGT GTG GTT CTC AAT GAA CAA CCT GAG TAC AGT GCA GTA | 738 |
| Lys Leu Ser Gly Val Val Leu Asn Glu Gln Pro Glu Tyr Ser Ala Val |     |
|         120             125             130                     |     |

| ATG AAG CAA ATA TTA GAA GAA TTC AAA AAT AGT AAG GGT TCC TAT ACT | 786 |
| Met Lys Gln Ile Leu Glu Glu Phe Lys Asn Ser Lys Gly Ser Tyr Thr |     |
|         135             140             145                     |     |

| GCA AAA ATT TTT AAA CTT ACT ACC ACT TTG ACT ATT CCT TAC TTT GGA | 834 |
| Ala Lys Ile Phe Lys Leu Thr Thr Thr Leu Thr Ile Pro Tyr Phe Gly |     |
|     150             155             160                         |     |

| CCA ACA GGA CCG AGT TGG CGG CTA ATT TGT CTT CCA GAA GAG CAC ACA | 882 |
| Pro Thr Gly Pro Ser Trp Arg Leu Ile Cys Leu Pro Glu Glu His Thr |     |
|     165             170             175                         |     |

| GAA AAG TGG AGA AAA TTT ATC TTT GTA TCT AAT CAT TGC ATG TCT GAT | 930 |
| Glu Lys Trp Arg Lys Phe Ile Phe Val Ser Asn His Cys Met Ser Asp |     |
| 180             185             190             195             |     |

| GGT CGG TCT TCG ATC CAC TTT TTT CAT GAT TTA AGA GAC GAA TTA AAT | 978 |
| Gly Arg Ser Ser Ile His Phe Phe His Asp Leu Arg Asp Glu Leu Asn |     |
|         200             205             210                     |     |

| AAT ATT AAA ACT CCA CCA AAA AAA TTA GAT TAC ATT TTC AAG TAC GAG | 1026 |
| Asn Ile Lys Thr Pro Pro Lys Lys Leu Asp Tyr Ile Phe Lys Tyr Glu |      |
|             215             220             225                 |      |

| GAG GAT TAC CAA TTA TTG AGG AAA CTT CCA GAA CCG ATC GAA AAG GTG | 1074 |
| Glu Asp Tyr Gln Leu Leu Arg Lys Leu Pro Glu Pro Ile Glu Lys Val |      |
|         230             235             240                     |      |

| ATA GAC TTT AGA CCA CCG TAC TTG TTT ATT CCG AAG TCA CTT CTT TCG | 1122 |
| Ile Asp Phe Arg Pro Pro Tyr Leu Phe Ile Pro Lys Ser Leu Leu Ser |      |
|     245             250             255                         |      |

```
GGT TTC ATC TAC AAT CAT TTG AGA TTT TCT TCA AAA GGT GTC TGT ATG        1170
Gly Phe Ile Tyr Asn His Leu Arg Phe Ser Ser Lys Gly Val Cys Met
260             265                 270                 275

AGA ATG GAT GAT GTG GAA AAA ACC GAT GAT GTT GTC ACC GAG ATC ATC        1218
Arg Met Asp Asp Val Glu Lys Thr Asp Asp Val Val Thr Glu Ile Ile
                280                 285                 290

AAT ATT TCA CCA ACA GAA TTT CAA GCG ATT AAA GCA AAT ATT AAA TCA        1266
Asn Ile Ser Pro Thr Glu Phe Gln Ala Ile Lys Ala Asn Ile Lys Ser
            295                 300                 305

AAT ATC CAA GGT AAG TGT ACT ATC ACT CCG TTT TTA CAT GTT TGT TGG        1314
Asn Ile Gln Gly Lys Cys Thr Ile Thr Pro Phe Leu His Val Cys Trp
        310                 315                 320

TTT GTA TCT CTT CAT AAA TGG GGT AAA TTT TTC AAA CCA TTG AAC TTC        1362
Phe Val Ser Leu His Lys Trp Gly Lys Phe Phe Lys Pro Leu Asn Phe
325                 330                 335

GAA TGG CTT ACG GAT ATT TTT ATC CCC GCA GAT TGC CGC TCA CAA CTA        1410
Glu Trp Leu Thr Asp Ile Phe Ile Pro Ala Asp Cys Arg Ser Gln Leu
340                 345                 350                 355

CCA GAT GAT GAT GAA ATG AGA CAG ATG TAC AGA TAT GGC GCT AAC GTT        1458
Pro Asp Asp Asp Glu Met Arg Gln Met Tyr Arg Tyr Gly Ala Asn Val
                360                 365                 370

GGA TTT ATT GAC TTC ACC CCC TGG ATA AGC GAA TTT GAC ATG AAT GAT        1506
Gly Phe Ile Asp Phe Thr Pro Trp Ile Ser Glu Phe Asp Met Asn Asp
            375                 380                 385

AAC AAA GAA AAT TTT TGG CCA CTT ATT GAG CAC TAC CAT GAA GTA ATT        1554
Asn Lys Glu Asn Phe Trp Pro Leu Ile Glu His Tyr His Glu Val Ile
        390                 395                 400

TCG GAA GCT TTA AGA AAT AAA AAG CAT CTC CAT GGC TTA GGG TTC AAT        1602
Ser Glu Ala Leu Arg Asn Lys Lys His Leu His Gly Leu Gly Phe Asn
    405                 410                 415

ATA CAA GGC TTC GTT CAA AAA TAT GTG AAC ATT GAC AAG GTA ATG TGC        1650
Ile Gln Gly Phe Val Gln Lys Tyr Val Asn Ile Asp Lys Val Met Cys
420                 425                 430                 435

GAT CGT GCC ATC GGG AAA AGA CGC GGA GGT ACA TTG TTA AGC AAT GTA        1698
Asp Arg Ala Ile Gly Lys Arg Arg Gly Gly Thr Leu Leu Ser Asn Val
                440                 445                 450

GGT CTG TTT AAT CAG TTA GAG GAG CCC GAT GCC AAA TAT TCT ATA TGC        1746
Gly Leu Phe Asn Gln Leu Glu Glu Pro Asp Ala Lys Tyr Ser Ile Cys
            455                 460                 465

GAT TTG GCA TTT GGC CAA TTT CAA GGA TCC TGG CAC CAA GCA TTT TCC        1794
Asp Leu Ala Phe Gly Gln Phe Gln Gly Ser Trp His Gln Ala Phe Ser
        470                 475                 480

TTG GGT GTT TGT TCG ACT AAT GTA AAG GGG ATG AAT ATT GTT GTT GCT        1842
Leu Gly Val Cys Ser Thr Asn Val Lys Gly Met Asn Ile Val Val Ala
    485                 490                 495

TCA ACA AAG AAT GTT GTT GGT AGT CAA GAA TCT CTC GAA GAG CTT TGC        1890
Ser Thr Lys Asn Val Val Gly Ser Gln Glu Ser Leu Glu Glu Leu Cys
500                 505                 510                 515

TCC ATT TAC AAA GCT CTC CTT TTA GGC CCT TAGATCTCAC ATGATGCTTG          1940
Ser Ile Tyr Lys Ala Leu Leu Leu Gly Pro
                520                 525

ACTGATATTA TTCGACAATA TGATTATGTC GTGT                                  1974
```

( 2 ) INFORMATION FOR SEQ ID NO:17:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Met | Asn | Glu | Ile | Asp | Glu | Lys | Asn | Gln | Ala | Pro | Val | Gln | Gln | Glu | Cys |
|---|---|---|---|---|---|---|---|---|---|---|---|---|---|---|---|
| 1 | | | | 5 | | | | | 10 | | | | | 15 | |
| Leu | Lys | Glu | Met | Ile | Gln | Asn | Gly | His | Ala | Arg | Arg | Met | Gly | Ser | Val |
| | | | 20 | | | | | 25 | | | | | 30 | | |
| Glu | Asp | Leu | Tyr | Val | Ala | Leu | Asn | Arg | Gln | Asn | Leu | Tyr | Arg | Asn | Phe |
| | | | 35 | | | | 40 | | | | | 45 | | | |
| Cys | Thr | Tyr | Gly | Glu | Leu | Ser | Asp | Tyr | Cys | Thr | Arg | Asp | Gln | Leu | Thr |
| | 50 | | | | | 55 | | | | | 60 | | | | |
| Leu | Ala | Leu | Arg | Glu | Ile | Cys | Leu | Lys | Asn | Pro | Thr | Leu | Leu | His | Ile |
| 65 | | | | | 70 | | | | | 75 | | | | | 80 |
| Val | Leu | Pro | Thr | Arg | Trp | Pro | Asn | His | Glu | Asn | Tyr | Tyr | Arg | Ser | Ser |
| | | | | 85 | | | | | 90 | | | | | 95 | |
| Glu | Tyr | Tyr | Ser | Arg | Pro | His | Pro | Val | His | Asp | Tyr | Ile | Ser | Val | Leu |
| | | | 100 | | | | | 105 | | | | | 110 | | |
| Gln | Glu | Leu | Lys | Leu | Ser | Gly | Val | Val | Leu | Asn | Glu | Gln | Pro | Glu | Tyr |
| | | | 115 | | | | 120 | | | | | 125 | | | |
| Ser | Ala | Val | Met | Lys | Gln | Ile | Leu | Glu | Glu | Phe | Lys | Asn | Ser | Lys | Gly |
| | 130 | | | | | 135 | | | | | 140 | | | | |
| Ser | Tyr | Thr | Ala | Lys | Ile | Phe | Lys | Leu | Thr | Thr | Thr | Leu | Thr | Ile | Pro |
| 145 | | | | | 150 | | | | | 155 | | | | | 160 |
| Tyr | Phe | Gly | Pro | Thr | Gly | Pro | Ser | Trp | Arg | Leu | Ile | Cys | Leu | Pro | Glu |
| | | | | 165 | | | | | 170 | | | | | 175 | |
| Glu | His | Thr | Glu | Lys | Trp | Arg | Lys | Phe | Ile | Phe | Val | Ser | Asn | His | Cys |
| | | | 180 | | | | | 185 | | | | | 190 | | |
| Met | Ser | Asp | Gly | Arg | Ser | Ser | Ile | His | Phe | Phe | His | Asp | Leu | Arg | Asp |
| | | | 195 | | | | | 200 | | | | | 205 | | |
| Glu | Leu | Asn | Asn | Ile | Lys | Thr | Pro | Pro | Lys | Lys | Leu | Asp | Tyr | Ile | Phe |
| | 210 | | | | | 215 | | | | | 220 | | | | |
| Lys | Tyr | Glu | Glu | Asp | Tyr | Gln | Leu | Leu | Arg | Lys | Leu | Pro | Glu | Pro | Ile |
| 225 | | | | | 230 | | | | | 235 | | | | | 240 |
| Glu | Lys | Val | Ile | Asp | Phe | Arg | Pro | Pro | Tyr | Leu | Phe | Ile | Pro | Lys | Ser |
| | | | | 245 | | | | | 250 | | | | | 255 | |
| Leu | Leu | Ser | Gly | Phe | Ile | Tyr | Asn | His | Leu | Arg | Phe | Ser | Ser | Lys | Gly |
| | | | 260 | | | | | 265 | | | | | 270 | | |
| Val | Cys | Met | Arg | Met | Asp | Asp | Val | Glu | Lys | Thr | Asp | Asp | Val | Val | Thr |
| | | 275 | | | | | 280 | | | | | 285 | | | |
| Glu | Ile | Ile | Asn | Ile | Ser | Pro | Thr | Glu | Phe | Gln | Ala | Ile | Lys | Ala | Asn |
| | 290 | | | | | 295 | | | | | 300 | | | | |
| Ile | Lys | Ser | Asn | Ile | Gln | Gly | Lys | Cys | Thr | Ile | Thr | Pro | Phe | Leu | His |
| 305 | | | | | 310 | | | | | 315 | | | | | 320 |
| Val | Cys | Trp | Phe | Val | Ser | Leu | His | Lys | Trp | Gly | Lys | Phe | Phe | Lys | Pro |
| | | | | 325 | | | | | 330 | | | | | 335 | |
| Leu | Asn | Phe | Glu | Trp | Leu | Thr | Asp | Ile | Phe | Ile | Pro | Ala | Asp | Cys | Arg |
| | | | 340 | | | | | 345 | | | | | 350 | | |
| Ser | Gln | Leu | Pro | Asp | Asp | Asp | Glu | Met | Arg | Gln | Met | Tyr | Arg | Tyr | Gly |
| | | | 355 | | | | | 360 | | | | | 365 | | |
| Ala | Asn | Val | Gly | Phe | Ile | Asp | Phe | Thr | Pro | Trp | Ile | Ser | Glu | Phe | Asp |
| | | 370 | | | | | 375 | | | | | 380 | | | |
| Met | Asn | Asp | Asn | Lys | Glu | Asn | Phe | Trp | Pro | Leu | Ile | Glu | His | Tyr | His |
| 385 | | | | | 390 | | | | | 395 | | | | | 400 |
| Glu | Val | Ile | Ser | Glu | Ala | Leu | Arg | Asn | Lys | Lys | His | Leu | His | Gly | Leu |
| | | | | 405 | | | | | 410 | | | | | 415 | |

5,658,777

39

40

-continued

| | | | | | | | | | | | | | | |
|---|---|---|---|---|---|---|---|---|---|---|---|---|---|---|
| Gly | Phe | Asn | Ile | Gln | Gly | Phe | Val | Gln | Lys | Tyr | Val | Asn | Ile | Asp | Lys |
| | | | 420 | | | | 425 | | | | | 430 | | |
| Val | Met | Cys | Asp | Arg | Ala | Ile | Gly | Lys | Arg | Arg | Gly | Gly | Thr | Leu | Leu |
| | | 435 | | | | 440 | | | | | 445 | | | | |
| Ser | Asn | Val | Gly | Leu | Phe | Asn | Gln | Leu | Glu | Glu | Pro | Asp | Ala | Lys | Tyr |
| | 450 | | | | | 455 | | | | 460 | | | | | |
| Ser | Ile | Cys | Asp | Leu | Ala | Phe | Gly | Gln | Phe | Gln | Gly | Ser | Trp | His | Gln |
| 465 | | | | 470 | | | | 475 | | | | | 480 | | |
| Ala | Phe | Ser | Leu | Gly | Val | Cys | Ser | Thr | Asn | Val | Lys | Gly | Met | Asn | Ile |
| | | | | 485 | | | | 490 | | | | | | 495 | |
| Val | Val | Ala | Ser | Thr | Lys | Asn | Val | Val | Gly | Ser | Gln | Glu | Ser | Leu | Glu |
| | | | 500 | | | | | 505 | | | | 510 | | | |
| Glu | Leu | Cys | Ser | Ile | Tyr | Lys | Ala | Leu | Leu | Leu | Gly | Pro | | | |
| | 515 | | | | | 520 | | | | | 525 | | | | |

( 2 ) INFORMATION FOR SEQ ID NO:18:

( i ) SEQUENCE CHARACTERISTICS:
( A ) LENGTH: 2080 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 311..1888

( x i ) SEQUENCE DESCRIPTION: SEQ ID NO:18:

```
CTTGAACATT GATCAATGTG AAATACTGAT TGTGATGTTC AATATATTTG CTGATCTTAG      60

GGTGATTGGT AACCAAAAAT GCCGTCGGGC ATTGTTCTAA AGGCTTGTGA TTTTGTAAGT     120

TTTTGATCG CCTATTGTTT TTGGGCTGGC ATCAGCATCG CGTGGAGCGA AGTCCAAATA      180

TGTTTTCTAT TGTTTTCAT GGCTCTTCGA AAGCGTCTT TTTTAAAGCC AACCCAACAA       240

AACTTGAGAC ATGGAAACAG AAGAAAGCCA ATTAGCAGT ATAACAAAAA TCATCAATCC      300
```

| AAAAACTCTA | ATG | AAT | ACC | TAC | AGT | GAA | AAA | ACG | TCT | CTT | GTT | CAA | GAT | 349 |
|---|---|---|---|---|---|---|---|---|---|---|---|---|---|---|
| | Met | Asn | Thr | Tyr | Ser | Glu | Lys | Thr | Ser | Leu | Val | Gln | Asp | |
| | 1 | | | | 5 | | | | | 10 | | | | |

| GAA | TGT | CTT | GTC | AAG | ATG | ATA | CAG | AAT | GGG | CAT | TCC | CGG | CGT | ATG | GGA | 397 |
|---|---|---|---|---|---|---|---|---|---|---|---|---|---|---|---|---|
| Glu | Cys | Leu | Val | Lys | Met | Ile | Gln | Asn | Gly | His | Ser | Arg | Arg | Met | Gly | |
| | 15 | | | | 20 | | | | | 25 | | | | | | |

| TCT | GTG | GAA | GAT | TTG | TAC | GCT | GCA | CTC | AAC | AGA | CAG | AAA | TTG | TAT | CGG | 445 |
|---|---|---|---|---|---|---|---|---|---|---|---|---|---|---|---|---|
| Ser | Val | Glu | Asp | Leu | Tyr | Ala | Ala | Leu | Asn | Arg | Gln | Lys | Leu | Tyr | Arg | |
| 30 | | | | | 35 | | | | 40 | | | | | | 45 | |

| AAT | TTT | TCG | ACA | TAT | TCA | GAG | CTG | AAT | GAT | TAC | TGT | ACC | AAA | GAT | CAG | 493 |
|---|---|---|---|---|---|---|---|---|---|---|---|---|---|---|---|---|
| Asn | Phe | Ser | Thr | Tyr | Ser | Glu | Leu | Asn | Asp | Tyr | Cys | Thr | Lys | Asp | Gln | |
| | | | 50 | | | | | 55 | | | | | 60 | | | |

| CTC | GCA | TTA | GCT | CTA | AGA | AAT | ATA | TGT | TTG | AAA | AAT | CCG | ACT | CTC | CTA | 541 |
|---|---|---|---|---|---|---|---|---|---|---|---|---|---|---|---|---|
| Leu | Ala | Leu | Ala | Leu | Arg | Asn | Ile | Cys | Leu | Lys | Asn | Pro | Thr | Leu | Leu | |
| | | | 65 | | | | | 70 | | | | | 75 | | | |

| CAT | ATT | GTA | TTA | CCG | GCA | AGA | TGG | CCA | GAT | CAT | GAA | AAG | TAT | TAC | CTT | 589 |
|---|---|---|---|---|---|---|---|---|---|---|---|---|---|---|---|---|
| His | Ile | Val | Leu | Pro | Ala | Arg | Trp | Pro | Asp | His | Glu | Lys | Tyr | Tyr | Leu | |
| | | 80 | | | | | 85 | | | | | 90 | | | | |

| AGC | TCA | GAA | TAT | TAT | TCA | CAG | CCC | CGT | CCA | AAA | CAT | GAT | TAT | ATT | TCG | 637 |
|---|---|---|---|---|---|---|---|---|---|---|---|---|---|---|---|---|
| Ser | Ser | Glu | Tyr | Tyr | Ser | Gln | Pro | Arg | Pro | Lys | His | Asp | Tyr | Ile | Ser | |
| | 95 | | | | | 100 | | | | | 105 | | | | | |

| GTT | TTG | CCT | GAG | TTG | AAA | TTA | GAT | GGT | GTG | ATT | CTC | AAC | GAG | CAA | CCT | 685 |
|---|---|---|---|---|---|---|---|---|---|---|---|---|---|---|---|---|
| Val | Leu | Pro | Glu | Leu | Lys | Leu | Asp | Gly | Val | Ile | Leu | Asn | Glu | Gln | Pro | |
| 110 | | | | | 115 | | | | 120 | | | | | | 125 | |

| GAG | CAC | AAT | GCC | CTA | ATG | AAG | CAA | ATA | CTA | GAA | GAA | TTT | GCG | AAT | AGC | 733 |
|---|---|---|---|---|---|---|---|---|---|---|---|---|---|---|---|---|

|  |  |  |  |  |  |  |  |  |  |  |  |  |  |  |  |
|---|---|---|---|---|---|---|---|---|---|---|---|---|---|---|---|
| Glu | His | Asn | Ala | Leu | Met | Lys | Gln | Ile | Leu | Glu | Glu | Phe | Ala | Asn | Ser |
|  |  |  |  | 130 |  |  |  |  | 135 |  |  |  |  | 140 |  |

```
AAT  GGA  TCT  TAT  ACT  GCA  AAA  ATC  TTT  AAA  TTG  ACC  ACC  GCT  TTG  ACT       781
Asn  Gly  Ser  Tyr  Thr  Ala  Lys  Ile  Phe  Lys  Leu  Thr  Thr  Ala  Leu  Thr
              145                    150                      155

ATA  CCT  TAC  ACT  GGG  CCA  ACA  AGT  CCA  ACT  TGG  CGG  TTG  ATT  TGT  CTC       829
Ile  Pro  Tyr  Thr  Gly  Pro  Thr  Ser  Pro  Thr  Trp  Arg  Leu  Ile  Cys  Leu
          160                    165                      170

CCA  GAA  GAA  GAT  GAC  ACG  AAT  AAG  TGG  AAG  AAA  TTT  ATA  TTT  GTA  TCC       877
Pro  Glu  Glu  Asp  Asp  Thr  Asn  Lys  Trp  Lys  Lys  Phe  Ile  Phe  Val  Ser
     175                      180                      185

AAT  CAC  TGC  ATG  TGC  GAT  GGT  AGA  TCC  TCA  ATT  CAC  TTT  TTT  CAG  GAT       925
Asn  His  Cys  Met  Cys  Asp  Gly  Arg  Ser  Ser  Ile  His  Phe  Phe  Gln  Asp
190                      195                      200                      205

CTA  AGA  GAT  GAA  TTA  AAC  AAC  ATA  AAA  ACT  CTG  CCA  AAG  AAA  TTG  GAC       973
Leu  Arg  Asp  Glu  Leu  Asn  Asn  Ile  Lys  Thr  Leu  Pro  Lys  Lys  Leu  Asp
                    210                      215                      220

TAC  ATT  TTC  GAG  TAC  GAA  AAG  GAT  TAC  CAA  CTT  TTG  AGA  AAG  CTC  CCA      1021
Tyr  Ile  Phe  Glu  Tyr  Glu  Lys  Asp  Tyr  Gln  Leu  Leu  Arg  Lys  Leu  Pro
               225                      230                      235

GAA  CCC  ATT  GAA  AAT  ATG  ATA  GAT  TTC  AGG  CCG  CCA  TAT  TTG  TTT  ATT      1069
Glu  Pro  Ile  Glu  Asn  Met  Ile  Asp  Phe  Arg  Pro  Pro  Tyr  Leu  Phe  Ile
          240                    245                      250

CCG  AAG  TCT  CTT  CTT  TCT  GGT  TTT  ATT  TAC  AGT  CAT  TTG  AGG  TTT  TCT      1117
Pro  Lys  Ser  Leu  Leu  Ser  Gly  Phe  Ile  Tyr  Ser  His  Leu  Arg  Phe  Ser
     255                    260                      265

TCA  AAG  GGT  GTT  TGC  ACG  AGA  ATG  GAT  GAG  ATA  GAA  AAA  AGT  GAT  GAG      1165
Ser  Lys  Gly  Val  Cys  Thr  Arg  Met  Asp  Glu  Ile  Glu  Lys  Ser  Asp  Glu
270                      275                      280                      285

ATT  GTT  ACA  GAA  ATT  ATC  AAT  ATT  TCT  CCA  TCA  GAG  TTT  CAA  AAA  ATT      1213
Ile  Val  Thr  Glu  Ile  Ile  Asn  Ile  Ser  Pro  Ser  Glu  Phe  Gln  Lys  Ile
                    290                      295                      300

AGA  ACG  AAA  ATT  AAA  TTA  AAC  ATT  CCC  GGT  AAG  TGC  ACC  ATC  ACT  CCG      1261
Arg  Thr  Lys  Ile  Lys  Leu  Asn  Ile  Pro  Gly  Lys  Cys  Thr  Ile  Thr  Pro
               305                      310                      315

TTC  TTA  GAA  GTT  TGT  TGG  TTT  GTT  ACT  CTC  CAT  AAA  TGG  GGC  AAG  TTT      1309
Phe  Leu  Glu  Val  Cys  Trp  Phe  Val  Thr  Leu  His  Lys  Trp  Gly  Lys  Phe
          320                    325                      330

TTC  AAA  CCA  CTG  AAG  TTC  GAG  TGG  CTC  ACT  GAT  GTT  TTT  ATA  CCT  GCA      1357
Phe  Lys  Pro  Leu  Lys  Phe  Glu  Trp  Leu  Thr  Asp  Val  Phe  Ile  Pro  Ala
     335                    340                      345

GAT  TGC  CGC  TCA  TTG  CTG  CCT  GAA  GAT  GAA  GAA  GTG  AGA  GCT  ATG  TAC      1405
Asp  Cys  Arg  Ser  Leu  Leu  Pro  Glu  Asp  Glu  Glu  Val  Arg  Ala  Met  Tyr
350                      355                      360                      365

AGG  TAC  GGC  GCT  AAC  GTT  GGG  TTT  GTT  GAC  TTC  ACT  CCA  TGG  ATA  AGC      1453
Arg  Tyr  Gly  Ala  Asn  Val  Gly  Phe  Val  Asp  Phe  Thr  Pro  Trp  Ile  Ser
                    370                      375                      380

AAA  TTC  AAC  ATG  AAC  GAC  AGC  AAA  GAA  AAT  TTC  TGG  CCA  CTT  ATT  GCA      1501
Lys  Phe  Asn  Met  Asn  Asp  Ser  Lys  Glu  Asn  Phe  Trp  Pro  Leu  Ile  Ala
               385                      390                      395

CAT  TAT  CAT  GAA  GTA  ATT  TCC  GGG  GCG  ATA  AAA  GAC  AAG  AAG  CAT  CTC      1549
His  Tyr  His  Glu  Val  Ile  Ser  Gly  Ala  Ile  Lys  Asp  Lys  Lys  His  Leu
          400                    405                      410

AAT  GGT  TTG  GGG  TTC  AAC  ATA  CAA  AGC  TTG  GTC  CAA  AAG  TAT  GTC  AAC      1597
Asn  Gly  Leu  Gly  Phe  Asn  Ile  Gln  Ser  Leu  Val  Gln  Lys  Tyr  Val  Asn
     415                    420                      425

ATT  GAT  AAA  GTA  ATG  CGT  GAT  CGT  GCT  CTT  GGT  AAA  TCA  CGT  GGG  GGC      1645
Ile  Asp  Lys  Val  Met  Arg  Asp  Arg  Ala  Leu  Gly  Lys  Ser  Arg  Gly  Gly
430                      435                      440                      445

ACT  TTG  TTG  AGC  AAC  GTA  GGT  ATG  TTC  CAC  CAA  TCG  GAG  GAG  ACC  GAA      1693
```

| | | | | | | | | | | | | | | | | |
|---|---|---|---|---|---|---|---|---|---|---|---|---|---|---|---|---|
| Thr | Leu | Leu | Ser | Asn | Val | Gly | Met | Phe | His | Gln | Ser | Glu | Glu | Thr | Glu | |
| | | | | 450 | | | | 455 | | | | | 460 | | | |

| | | | | | | | | | | | | | | | | |
|---|---|---|---|---|---|---|---|---|---|---|---|---|---|---|---|---|
| CAC | AAG | TAT | CGT | ATA | AGA | GAT | TTG | GCC | TTT | GGT | CAA | TTT | CAA | GGG | TCA | 1741 |
| His | Lys | Tyr | Arg | Ile | Arg | Asp | Leu | Ala | Phe | Gly | Gln | Phe | Gln | Gly | Ser | |
| | | | 465 | | | | 470 | | | | 475 | | | | | |
| TGG | CAT | CAA | GCT | TTT | TCA | TTG | GGT | GTT | TCT | TCG | ACT | AAT | GTG | AAG | GGA | 1789 |
| Trp | His | Gln | Ala | Phe | Ser | Leu | Gly | Val | Ser | Ser | Thr | Asn | Val | Lys | Gly | |
| | | 480 | | | | | 485 | | | | | 490 | | | | |
| ATG | AAC | ATT | TTG | ATT | TCT | TCA | ACG | AAA | AAT | GTC | GTG | GGT | AGT | CAA | GAA | 1837 |
| Met | Asn | Ile | Leu | Ile | Ser | Ser | Thr | Lys | Asn | Val | Val | Gly | Ser | Gln | Glu | |
| | 495 | | | | | 500 | | | | | 505 | | | | | |
| TTG | TTG | GAG | GAA | CTT | TGT | GCT | ATG | TAC | AAG | GCT | CTG | CTT | TTA | AAT | CCC | 1885 |
| Leu | Leu | Glu | Glu | Leu | Cys | Ala | Met | Tyr | Lys | Ala | Leu | Leu | Leu | Asn | Pro | |
| 510 | | | | | 515 | | | | 520 | | | | | 525 | | |

```
TGATTCTTCT AAGACAATAT GATGGTGGAT ACCTTAAAA ATTATAGTTA TATTGTAGGG    1945
CTATCCTGTT TTGATATTAT AATGTTTTTT TAGCTTGTAG AGAGAAATGG TATCAGTTTC   2005
TTTTACTAAG ATTCGAACTA ATCAATATCT CAAAGTGATT AAACGACGTG TGTAAGGTAA   2065
GTAAGTGTAC AGAAA                                                   2080
```

( 2 ) INFORMATION FOR SEQ ID NO:19:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| | | | | | | | | | | | | | | | |
|---|---|---|---|---|---|---|---|---|---|---|---|---|---|---|---|
| Met | Asn | Thr | Tyr | Ser | Glu | Lys | Thr | Ser | Leu | Val | Gln | Asp | Glu | Cys | Leu |
| 1 | | | | 5 | | | | | 10 | | | | | 15 | |
| Val | Lys | Met | Ile | Gln | Asn | Gly | His | Ser | Arg | Arg | Met | Gly | Ser | Val | Glu |
| | | | 20 | | | | | 25 | | | | 30 | | | |
| Asp | Leu | Tyr | Ala | Ala | Leu | Asn | Arg | Gln | Lys | Leu | Tyr | Arg | Asn | Phe | Ser |
| | | | 35 | | | | 40 | | | | | 45 | | | |
| Thr | Tyr | Ser | Glu | Leu | Asn | Asp | Tyr | Cys | Thr | Lys | Asp | Gln | Leu | Ala | Leu |
| | 50 | | | | | 55 | | | | | 60 | | | | |
| Ala | Leu | Arg | Asn | Ile | Cys | Leu | Lys | Asn | Pro | Thr | Leu | Leu | His | Ile | Val |
| 65 | | | | | 70 | | | | | 75 | | | | | 80 |
| Leu | Pro | Ala | Arg | Trp | Pro | Asp | His | Glu | Lys | Tyr | Tyr | Leu | Ser | Ser | Glu |
| | | | | 85 | | | | | 90 | | | | | 95 | |
| Tyr | Tyr | Ser | Gln | Pro | Arg | Pro | Lys | His | Asp | Tyr | Ile | Ser | Val | Leu | Pro |
| | | | 100 | | | | | 105 | | | | | 110 | | |
| Glu | Leu | Lys | Leu | Asp | Gly | Val | Ile | Leu | Asn | Glu | Gln | Pro | Glu | His | Asn |
| | | 115 | | | | | 120 | | | | | 125 | | | |
| Ala | Leu | Met | Lys | Gln | Ile | Leu | Glu | Glu | Phe | Ala | Asn | Ser | Asn | Gly | Ser |
| | 130 | | | | | 135 | | | | | 140 | | | | |
| Tyr | Thr | Ala | Lys | Ile | Phe | Lys | Leu | Thr | Thr | Ala | Leu | Thr | Ile | Pro | Tyr |
| 145 | | | | | 150 | | | | | 155 | | | | | 160 |
| Thr | Gly | Pro | Thr | Ser | Pro | Thr | Trp | Arg | Leu | Ile | Cys | Leu | Pro | Glu | Glu |
| | | | | 165 | | | | | 170 | | | | | 175 | |
| Asp | Asp | Thr | Asn | Lys | Trp | Lys | Lys | Phe | Ile | Phe | Val | Ser | Asn | His | Cys |
| | | | 180 | | | | | 185 | | | | | 190 | | |
| Met | Cys | Asp | Gly | Arg | Ser | Ser | Ile | His | Phe | Phe | Gln | Asp | Leu | Arg | Asp |
| | | 195 | | | | | 200 | | | | | 205 | | | |
| Glu | Leu | Asn | Asn | Ile | Lys | Thr | Leu | Pro | Lys | Lys | Leu | Asp | Tyr | Ile | Phe |
| | 210 | | | | | 215 | | | | | 220 | | | | |

```
Glu Tyr Glu Lys Asp Tyr Gln Leu Leu Arg Lys Leu Pro Glu Pro Ile
225             230             235             240

Glu Asn Met Ile Asp Phe Arg Pro Pro Tyr Leu Phe Ile Pro Lys Ser
            245             250             255

Leu Leu Ser Gly Phe Ile Tyr Ser His Leu Arg Phe Ser Ser Lys Gly
            260             265             270

Val Cys Thr Arg Met Asp Glu Ile Glu Lys Ser Asp Glu Ile Val Thr
        275             280             285

Glu Ile Ile Asn Ile Ser Pro Ser Glu Phe Gln Lys Ile Arg Thr Lys
    290             295             300

Ile Lys Leu Asn Ile Pro Gly Lys Cys Thr Ile Thr Pro Phe Leu Glu
305             310             315             320

Val Cys Trp Phe Val Thr Leu His Lys Trp Gly Lys Phe Phe Lys Pro
            325             330             335

Leu Lys Phe Glu Trp Leu Thr Asp Val Phe Ile Pro Ala Asp Cys Arg
            340             345             350

Ser Leu Leu Pro Glu Asp Glu Glu Val Arg Ala Met Tyr Arg Tyr Gly
        355             360             365

Ala Asn Val Gly Phe Val Asp Phe Thr Pro Trp Ile Ser Lys Phe Asn
370             375             380

Met Asn Asp Ser Lys Glu Asn Phe Trp Pro Leu Ile Ala His Tyr His
385             390             395             400

Glu Val Ile Ser Gly Ala Ile Lys Asp Lys Lys His Leu Asn Gly Leu
            405             410             415

Gly Phe Asn Ile Gln Ser Leu Val Gln Lys Tyr Val Asn Ile Asp Lys
            420             425             430

Val Met Arg Asp Arg Ala Leu Gly Lys Ser Arg Gly Gly Thr Leu Leu
        435             440             445

Ser Asn Val Gly Met Phe His Gln Ser Glu Glu Thr Glu His Lys Tyr
    450             455             460

Arg Ile Arg Asp Leu Ala Phe Gly Gln Phe Gln Gly Ser Trp His Gln
465             470             475             480

Ala Phe Ser Leu Gly Val Ser Ser Thr Asn Val Lys Gly Met Asn Ile
            485             490             495

Leu Ile Ser Ser Thr Lys Asn Val Val Gly Ser Gln Glu Leu Leu Glu
        500             505             510

Glu Leu Cys Ala Met Tyr Lys Ala Leu Leu Leu Asn Pro
        515             520             525
```